United States Patent
Francko et al.

(10) Patent No.: US 8,580,708 B2
(45) Date of Patent: Nov. 12, 2013

(54) PLANT CRYOPROTECTANT COMPOSITIONS AND METHODS OF USE

(75) Inventors: David Francko, Tuscaloosa, AL (US); Kenneth G. Wilson, Lititz, PA (US); Qingshun Quinn Li, Centerville, OH (US); Maria Alejandra Equiza, Edmonton (CA)

(73) Assignee: Board of Trustees of the University of Alabama, Tuscaloosa, AL (US)

( * ) Notice: Subject to any disclaimer, the term of this patent is extended or adjusted under 35 U.S.C. 154(b) by 335 days.

(21) Appl. No.: 12/664,968

(22) PCT Filed: Jun. 17, 2008

(86) PCT No.: PCT/US2008/067241
§ 371 (c)(1),
(2), (4) Date: May 25, 2010

(87) PCT Pub. No.: WO2008/157555
PCT Pub. Date: Dec. 24, 2008

(65) Prior Publication Data
US 2010/0255991 A1    Oct. 7, 2010

Related U.S. Application Data

(60) Provisional application No. 61/124,824, filed on Jun. 18, 2007, provisional application No. 61/019,713, filed on Jan. 8, 2008.

(51) Int. Cl.
| | | |
|---|---|---|
| *A01N 63/00* | (2006.01) | |
| *A01N 27/00* | (2006.01) | |
| *A01N 31/00* | (2006.01) | |
| *A01N 33/00* | (2006.01) | |
| *A01N 37/00* | (2006.01) | |
| *A01N 47/10* | (2006.01) | |
| *A01N 55/08* | (2006.01) | |
| *A01N 43/00* | (2006.01) | |
| *A01N 59/16* | (2006.01) | |
| *A01N 59/06* | (2006.01) | |

(52) U.S. Cl.
USPC ........... 504/118; 504/121; 504/124; 504/125; 504/129; 504/142; 504/143; 504/193; 504/209; 504/300; 504/307; 504/326; 504/353; 504/357

(58) Field of Classification Search
USPC ......... 504/118, 121, 124, 125, 129, 142, 143, 504/193, 209, 300, 307, 326, 353, 357
See application file for complete search history.

(56) References Cited

U.S. PATENT DOCUMENTS 4,464,292 A    8/1984  Lengyel
5,504,054 A *  4/1996  Murphy ........................ 504/206
(Continued)

FOREIGN PATENT DOCUMENTS

WO    WO00/42843 A1    7/2000
WO    WO00/42843 A1 *  7/2000    ............. A01N 25/04

OTHER PUBLICATIONS del Amor et al., Environmental Control and Farm Management in Protected Cultivation, HortiModel, 2006, ISHS Acta Horticulturae, 718 III, International Symposium on Models for Plant Growth.*

(Continued)

*Primary Examiner* — Jane C Osweski
(74) *Attorney, Agent, or Firm* — Meunier Carlin & Curfman, LLC

(57) ABSTRACT

The present disclosure relates to cryoprotection of plants. The compositions and methods disclosed herein provide a means for protecting plants from frost or freeze damage or death due to sudden exposure to low temperature conditions. The present disclosure further relates to methods for providing cryoprotection to plants.

45 Claims, 1 Drawing Sheet

(56) References Cited

U.S. PATENT DOCUMENTS

| | | | |
|---|---|---|---|
| 5,653,054 | A | 8/1997 | Savignano et al. |
| 5,698,046 | A * | 12/1997 | St. Laurent et al. ......... 134/25.2 |
| 5,800,978 | A * | 9/1998 | Goodrich et al. ................ 435/2 |
| 6,235,683 | B1 | 5/2001 | Glenn et al. |
| 6,284,709 | B1 * | 9/2001 | Ju et al. ......................... 504/123 |
| 6,395,467 | B1 * | 5/2002 | Fahy et al. ..................... 435/1.3 |
| 2006/0142158 | A1 * | 6/2006 | Nonomura .................... 504/101 |

OTHER PUBLICATIONS

Francko et al., "A Topical Spray to Enhance Plant Resistance to Cold Injury and Mortality," HortTechnology, 21(1):109-118 (2011).

PCT/US2008/067241, Sep. 29, 2008, International Search Report and Written Opinion.

PCT/US2008/067241, Dec. 22, 2009, International Preliminary Report on Patentability.

Berestovsky, et al., Through Pore Diameter in the Cell Wall of Chara coralline. J. Exp. Botany 2001, vol. 52, No. 359, 1173-1177, p. 1173.

Del Amor, et al. 'The Effect of Antitranspirant on Growth and Water Uptake of Sweet Pepper Plants: Experiments and Empirical Modelling.', in ISHS Acta Horticulturae 718: III International Symposium on Models for Plant Growth, Environmental Control and Farm Management in Protected Cultivation (HortiModel 2006), abstract.

Francko et al., "A New Way to Test for Palm Cold Hardiness," Hardy Palm Internat., 58:26-29 (2004).

Francko et al., "Cold-Hardy Palms in Southwestern Ohio: Winter Damage, Mortality and Recovery," Palms, 46(1):5-13 (2002).

Larcher et al., "Persistent Supercooling and Silica Deposition in Cell Walls of Palm Leaves," Journal of Plant Physiol., 139:146-154 (1991).

Lee, "Principles of Insect Low Temperature Tolerance," Lee, R.E. and D. L. Denlinger (eds.), Insects at Low Temperature, Chapman and Hall, New York, pp. 17-46 (1991).

Lokuge, "Tissue Culture, Genetic Transformation and Cold Tolerance Mechanisms in Cold-Hardy Palms," Ph.D. Dissertation, Miami University (2006).

Maxwell et al., "Chlorophyll Fluorescence—A Practical Guide," Journal of Experimental Botany, 51(345):659-668 (2000).

Percival et al., "An Assessment of the Freezing Tolerance of Urban Trees Using Chlorophyll Fluorecence," Journal Hort. Sci. & Biotech., 78(2):254-260 (2003).

PQ Corporation, "AgSil® Potassium Silicate: Soluble Silicate for Agriculture," PQ Corporation Report 24, Valley Forge, Pennsylvania (2003).

Rizza et al., "Use of Chlorophyll Fluorescence to Evaluate the Cold Acclimation and Freezing Tolerance of Winter and Spring Oats," Plant Breeding, 120:389-396 (2001).

Tipping et al., "Efficay of Silwet L-77 Against Several Anthropod Pests of Common Table Grape," Journal of Econ. Entomol., 96(1):246-250 (2003).

Van Der Weele et al., "Growth of *Arabidopsis thaliana* Seedlings Under Water Deficit Studied by Control of Water Potential in Nutrient-Agar Media," Journal of Experimental Botany, 51(350):1555-1562 (2000).

Van Kooten et al., "The use of chlorophyll fluorescence nomenclature in plant stress physiology," Photosynthesis Research 25:147-150 (1990).

Versules et al., "LWR1 and LWR2 are Required for Osmoregulation and Osmotic Adjustment in *Arabidopsis*," Plant Physiology, 136:2831-2842 (2004).

\* cited by examiner

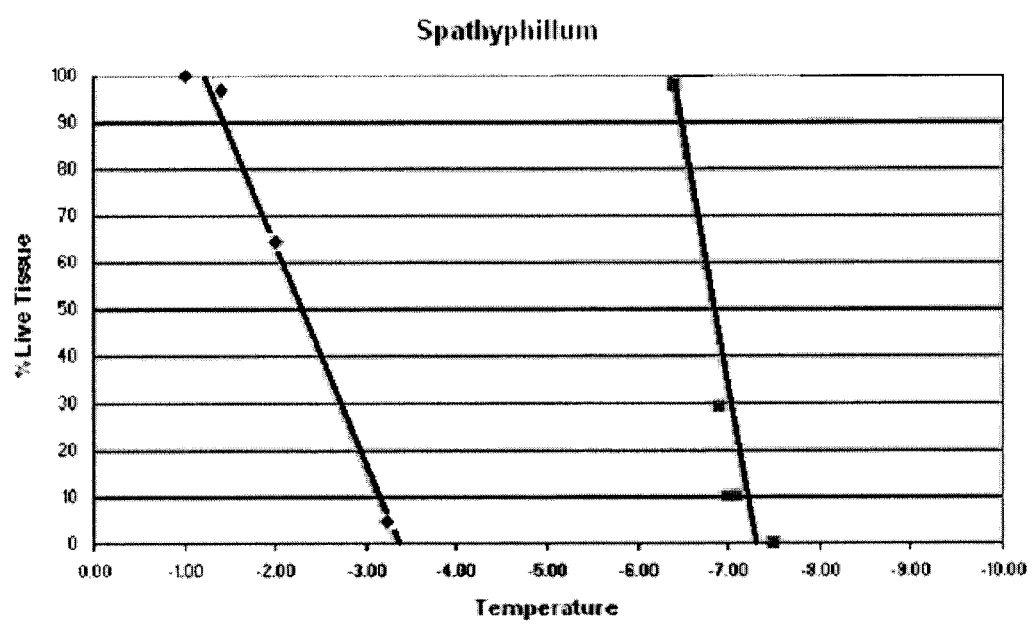

PLANT CRYOPROTECTANT COMPOSITIONS AND METHODS OF USE

CROSS REFERENCE TO RELATED APPLICATIONS

The present application claims the benefit of priority to U.S. Provisional Application Ser. No. 61/124,824, which was originally filed as a U.S. Non-provisional application Ser. No. 11/820,122 on Jun. 18, 2007 and subsequently converted on May 29, 2008 under 37 C.F.R. §1.53(c)(2) to a Provisional Application under U.S.C. §111(b) and 37 C.F.R. §1.53(c); and U.S. Provisional Application Ser. No. 61/019,713, filed Jan. 8, 2008, the contents of both of which are incorporated by reference in their entireties.

FIELD OF THE DISCLOSURE

The present disclosure relates to cryoprotection of plants. The compositions and methods disclosed herein provide a means for protecting plants from frost or freeze damage or death due to sudden exposure to low temperature conditions. The present disclosure further relates to methods for providing cryoprotection to plants.

BACKGROUND

Mankind's ability to control the earth's vegetation has been a key focus of civilization. Agriculturalists and horticulturalists have not only devoted their time and energy to the study of increasing plant yields and vitality, providing drought and insect resistance, but also to providing plants with resistance to the periodic exposure to unusually cold temperature conditions—conditions that are outside the control of man.

Plants have evolved to be compatible with their native environment. However, people have always sought to adapt and enjoy plants outside of their native areas, for example, as ornamental decoration, as landscaping, or a food source. Man has therefore developed methods and techniques that allow plants to thrive in locations that are well outside the climatic zones where a plant naturally occurs. For example, greenhouses allow for controlled germination and protected early growth of plants therefore increasing their chances of long term survival. But once outside the control of these special conditions, the plant becomes susceptible to conditions that can be unnatural to the species or to conditions to which the species is ill adapted. This is especially true for ornamental plants such as palms that have become popular both as additions to décor, but that are also cultivated by a growing number of people as house plants, patio plants, and as landscape additions. Therefore, once transplanted or otherwise outside the protection of a green house, for example, in a storage area before being sold to a consumer, the sudden onset of cold temperatures beyond those to which the plant has naturally adapted, can cause injury or death to the plant.

As a guide to horticulturists, the United States Department of Agriculture has developed Plant Hardiness Zone maps for plants based on the average annual minimum temperature a given area experiences. Although these Zones do not take soil, rainfall, and other variables into consideration, they are extremely useful because winter low temperatures are the most significant environmental factor governing plant hardiness. Although developed for use in the United States, these same Zone designations are now used worldwide to classify areas into Hardiness Zones and to classify plant species on the basis of their Zone Hardiness.

| USDA Zone | Average Annual Minimum Temperature (° C.) |
| --- | --- |
| 1 | −45.6 and colder |
| 2 | −40.0 to −45.5 |
| 3 | −34.5 to −39.9 |
| 4 | −28.9 to −34.4 |
| 5 | −23.4 to −28.8 |
| 6 | −17.8 to −23.3 |
| 7 | −12.3 to −17.7 |
| 8 | −6.7 to −12.2 |
| 9 | −1.2 to −6.6 |
| 10 | 4.4 to −1.1 |
| 11 | 10.0 to 5.5 |

Most of the continental United States and Eurasia are included in Zones 2 through 10. For example, if a plant is classified as hardy from Zone 5 through Zone 7, it means that it will likely grow well in Zones 5, 6, and 7, and that winter minimum temperatures much colder than the norm in Zone 5 could cause damage and for mortality. Importantly, winter care practices and technologies can extend the effective USDA range of plant species.

Although some plants can slowly adapt to low temperature conditions, the risk of losing large established plants due to frost/freeze conditions is of concern to both those who cultivate and sell plants, as well as to those who grow and nurture plants for their own personal use. In addition, fruit trees are especially susceptible to sudden frost/freeze events. The loss of a fruit crop or a major part of the foliage of fruit trees has a far reaching economic impact.

There is therefore a need for methods and compositions for protecting plants across all species against the sudden and damaging effects of cold weather conditions. The present disclosure meets these, as well as other, needs.

SUMMARY

In accordance with the purposes of the disclosed materials, compounds, compositions, articles, and methods, as embodied and broadly described herein, the disclosed subject matter, in one aspect, relates to compounds and compositions and methods for preparing and using such compounds and compositions. In a further aspect, the disclosed subject matter relates to compositions that comprise several components for providing cryoprotection to plants, for example, by protecting the intracellular structure, as well as the extracellular structure without affecting cellular biology or plant morphology. Methods of making and using these compositions are also disclosed.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURE

The accompanying FIGURE, which is incorporated in and constitutes a part of this specification, illustrates several aspects described below.

FIG. 1 is a graph that indicates the linear relationship between exposure temperature and the percentage of live leaf tissue remaining after 24 hours in whole excised leaves of

*Spathiphyllum* sp. (peace lily). Controls (♦) were sprayed with tap water and treated leaves (■) were sprayed with the composition No. 42 from Table 9 approximately 30 minutes prior to cold treatment.

DETAILED DISCLOSURE

The materials, compounds, compositions, articles, and methods described herein may be understood more readily by reference to the following detailed description of specific aspects of the disclosed subject matter and the Examples included therein and to the FIGURE.

Before the present materials, compounds, compositions, articles, and methods are disclosed and described, it is to be understood that the aspects described below are not limited to specific synthetic methods or specific reagents, as such may, of course, vary. It is also to be understood that the terminology used herein is for the purpose of describing particular aspects only and, unless a particular term is specifically defined herein, is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

DEFINITIONS

In this specification and in the claims that follow, reference will be made to a number of terms that shall be defined to have the following meanings:

Throughout this specification, unless the context requires otherwise, the word "comprise," or variations such as "comprises" or "comprising," will be understood to imply the inclusion of a stated integer or step or group of integers or steps but not the exclusion of any other integer or step or group of integers or steps.

It must be noted that, as used in the specification and the appended claims, the singular forms "a," "an" and "the" include plural referents unless the context clearly dictates otherwise.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that these data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

A weight percent of a component, unless specifically stated to the contrary, is based on the total weight of the formulation or composition in which the component is included.

By "contacting" is meant an instance of close physical contact of at least one substance to another substance.

By "sufficient amount" and "sufficient time" means an amount and time needed to achieve the desired result or results, e.g., dissolve a portion of the polymer.

"Biocompatible" as used herein means the biological response to the material or device is appropriate for the device's intended application in vivo. Any metabolites of these materials should also be biocompatible.

"Admixture" or "blend" is generally used herein means a physical combination of two or more different components. In the case of polymers, an admixture, or blend, of polymers is a physical blend or combination of two or more different polymers as opposed to a copolymer which is single polymeric material that is comprised of two or more different monomers.

"Absorbable" as used herein means the complete degradation of a material in vivo, and elimination of its metabolites from an animal or human subject.

"Molecular weight" as used herein, unless otherwise specified, refers generally to the relative average chain length of the bulk polymer. In practice, molecular weight can be estimated or characterized in various ways including gel permeation chromatography (GPC) or capillary viscometry. GPC molecular weights are reported as the weight-average molecular weight (Mw) as opposed to the number-average molecular weight (Mn). Capillary viscometry provides estimates of molecular weight as the Inherent Viscosity determined from a dilute polymer solution using a particular set of concentration, temperature, and solvent conditions.

"Bioactive agent" is used herein to include a compound of interest contained in or on the microparticle such as therapeutic or biologically active compounds. Examples can include, but are not limited to, drugs, small-molecule drugs, peptides, proteins, oligonucleotides. "Bioactive agent" includes a single such agent and is also intended to include a plurality of bioactive agents including, for example, combinations of 2 or more bioactive agents.

"Excipient" is used herein to include any other compound that can be contained in or on the microparticle that is not a therapeutically or biologically active compound. As such, an excipient should be pharmaceutically or biologically acceptable or relevant (for example, an excipient should generally be non-toxic to the subject). "Excipient" includes a single such compound and is also intended to include a plurality of excipients.

"Agent" is used herein to refer generally to compounds that are contained in or on a microparticle composition. Agent can include a bioactive agent or an excipient. "Agent" includes a single such compound and is also intended to include a plurality of such compounds.

The term "foliar damage threshold" or FDT is defined herein as the coldest temperature at which, 24 hours after cold exposure, 0% leaf damage is observed.

The term "foliar mortality threshold" or FMT is defined herein as the warmest temperature at which, 24 hours after cold exposure, 100% leaf damage is observed.

The term "provides cryoprotection in a manner capable of allowing a species to be planted in a lower zone" is defined herein as protection against freeze/frost sufficient that a plant can be protected in a colder USDA Zone. For example a plant designated as a Zone 10 plant can be successfully grown in Zone 9.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, amino, carboxylic acid, ester, ether, halide, hydroxy, ketone, azide, nitro, silyl, sulfo-oxo, or thiol, as described herein. A "lower alkyl" group is an alkyl group containing from one to six carbon atoms.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "polyalkylene group" as used herein is a group having two or more $CH_2$ groups linked to one another. The polyalkylene group can be represented by the formula —$(CH_2)_x$—, where "x" is an integer further defined herein.

The term "alkoxy" as used herein is an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or —$OA^1$-$(OA^2)_a$-$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This may be presumed in structural formulae herein wherein an asymmetric alkene is present, or it may be explicitly indicated by the bond symbol C=C. The alkenyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, substituted or unsubstituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The terms "amine" or "amino" as used herein are represented by the formula $NA^1A^2A^3$, where $A^1$, $A^2$, and $A^3$ can be, independently, hydrogen or substituted or unsubstituted alkyl, cycloalkyl, alkenyl, cycloalkenyl, alkynyl, cycloalkynyl, aryl, or heteroaryl group described above.

The term "carboxylic acid" as used herein is represented by the formula —C(O)OH.

The term "ester" as used herein is represented by the formula —OC(O)$A^1$ or —C(O)O$A^1$, where $A^1$ can be a substituted or unsubstituted alkyl, cycloalkyl, alkenyl, cycloalkenyl, alkynyl, cycloalkynyl, aryl, or heteroaryl group described above. The term "polyester" as used herein is represented by the formula $-(A^1O(O)C-A^2-C(O)O)_a-$ or $-(A^1O(O)C-A^2-OC(O))_a-$, where $A^1$ and $A^2$ can be, independently, a substituted or unsubstituted alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "halide" as used herein refers to the halogens fluorine, chlorine, bromine, and iodine.

The term "hydroxyl" as used herein is represented by the formula —OH.

The term "ketone" as used herein is represented by the formula $A^1C(O)A^2$, where $A^1$ and $A^2$ can be, independently, a substituted or unsubstituted alkyl, cycloalkyl, alkenyl, cycloalkenyl, alkynyl, cycloalkynyl, aryl, or heteroaryl group described above.

The term "azide" as used herein is represented by the formula —$N_3$.

The term "nitro" as used herein is represented by the formula —$NO_2$.

The term "nitrile" as used herein is represented by the formula —CN.

The term "silyl" as used herein is represented by the formula —$SiA^1A^2A^3$, where $A^1$, $A^2$, and $A^3$ can be, independently, hydrogen or a substituted or unsubstituted alkyl, cycloalkyl, alkoxy, alkenyl, cycloalkenyl, alkynyl, cycloalkynyl, aryl, or heteroaryl group described above.

Reference will now be made in detail to specific aspects of the disclosed materials, compounds, compositions, articles, and methods, examples of which are illustrated in the accompanying Examples and FIGURE.

Compositions and Methods

The disclosed compositions can be used to accomplish one or more of the following:
A) reduce the temperature at which foliage and flowers first become damaged by cold temperatures;
B) reduce the temperature at which foliage and flowers are completely killed by cold temperatures;
C) increase foliar cold resistance, for both first damage and kill, in an amount of from about 1.3° C. to about 5.2° C.;
D) protect plants by using multiple freeze avoidance mechanisms, both colligative and non-colligative mechanisms:
   i) utilizing an extracellular component that reduces cell and cell wall water by cytorrhysis without causing plasmolytic damage;
   ii) utilizing an extracellular component that also stabilizes cell membranes against ice crystal damage;
   iii) utilizing a colligative intracellular freezing point depressant;
E) increase plant cell strength by using stabilized and easily absorbable source of silicate that enhances transport of actives across cell membranes and strengthens cell walls against ice crystal damage;
F) provides protection against plant cell desiccation; and
G) efficiently deliver active agents thereby eliminating the need for high concentrations of active agents that can cause induced plant senescence and epinasty.

The ability of plants to withstand frost or freezes is genetically determined, and cold-tolerant plants, like their animal counterparts, are capable of numerous cold acclimation strategies. These cold acclimation strategies can be grouped into two large, interrelated functional subheadings: freeze tolerance and freeze avoidance. Freeze avoidance mechanisms include a variety of cryoprotectant molecules and other strategies that lower the intracellular freezing temperature (i.e., supercooling). Freeze tolerance mechanisms involve structural, anatomical, and biochemical adaptations to prevent or minimized damage to cells and tissues caused by ice formation.

Most cold-tolerant plants feature elements of both freeze avoidance and freeze tolerance strategies. For example, some cold tolerant palms are capable of surviving temperatures well below minus 12° C. and exhibit significant constitutive foliar cold-resistance capability. However, enhanced cold tolerance, for example, an additional 3° C. to 6° C. decrease in temperature, can be rapidly induced by exposure to chilling temperature. Indeed, the rapid time frame for cold acclimation (hours) induces a supercooling mechanism. The present disclosure takes advantage of this discovery by providing compositions which enhance the plants' own ability to provide self-cryoprotection by avoiding destructive plasmolysis and ice crystal formation.

Most commercially available cryoprotectants function by increasing the solute content of extracellular water and/or intracellular cytoplasm that has the effect of lowering the freezing point of these aqueous based compositions. Because excessively high solute concentrations are potentially toxic to cells and can induce irreversible plasmolytic water loss from cell interiors, the compositions disclosed herein comprise ingredients that are effective in producing the desired effects at concentrations well tolerated by plants.

The disclosed compositions can comprise intracellular cryoprotectants, as well as extracellular cryoprotectants.

In addition, the disclosed compositions can provide for a more robust plant cell wall by providing the plant with a compatible and easily absorbable source of silicate. Silicon is the second most abundant element in the earth's crust and is also abundant in some, but not all, soils. It is readily taken up by plants and in silicate rich soils is often present in relatively high concentrations in plant tissues. Silicon concentrations in plant tissues sometimes even exceed the concentrations of nitrogen and potassium. Therefore, silicon, in the form of silicate, is often a major constituent of plant tissue growth enhancers for plants growing in silicate-deficient soils; although, it is not considered to be an essential nutrient for terrestrial plants in general. Silicon has been shown to be a beneficial element for many, and, under certain conditions, perhaps most terrestrial plants. Silicate fertilizers are essential to the growth of important food crops such as rice. The beneficial effects of exposure to adequate silicate include decreased susceptibility to fungal pathogens (and insects), amelioration of abiotic stresses, and increased growth in some plants, and, importantly increased resistance to drought and cold.

Palms, both fruit bearing and decorative, as well as orchard trees, inter alia, lemons, limes, grapefruit, and oranges, and herbaceous fruit-bearing ornamentals (e.g., bananas) can suffer damage and/or death if exposed to sudden frost/freeze conditions. Many palms serve as decorations in locations, for example, restaurants, lobbies, and the like, that are located well outside their native agricultural zones. Moreover, many of these trees are either planted in the ground or potted, and those that are potted are often too large to be brought indoors when cold temperatures are forecast.

In addition, many species of subtropical flowers or shrubs have been used in institutional landscaping and in private homes and gardens. These plants, when exposed to sudden and rare cold temperature stress, will either die or be severely damaged.

The susceptibility of plants to damage or death due to cold is species dependent. Some species will tolerate temperatures below 0° C. while other species will succumb to frost damage or freeze death at temperatures above freezing. In addition, the mechanism by which plants die due to exposure to low temperatures is not ubiquitous.

The present disclosure takes into account the variability of plant species, for example, the morphology of the plant itself, including cellular structure, transpiration rates, and the susceptibility towards chemical treatments which are known to induce senescence, epinasty, or other undesirable effects.

Most plants have waxy cuticles which resist wetting. In the past surfactants have been used to deliver active ingredients to plants for the control of pathogens or insects. In many instances these commercial surfactants were either toxic to a particular species or were present in the formulation at such high concentrations that the treatment was not rendered economically viable on a scale greater than personal use.

Extracellular Desiccants

The compositions disclosed herein comprise one or more extracellular desiccants; agents that enter the tissues of plants but are too massive to readily pass across the cell membrane and therefore remain in extracellular compartments. By remaining in the extracellular spaces, the desiccants disclosed herein assist in gradually lowering the water content of the plants cells preparing the plant tissue for the onset of rapid freeze conditions (typically several hours). This allows the plant cells not to suffer loss of organelle integrity due to freeze-drying of the cell. Importantly, the desiccants disclosed herein allow for protection against freeze-drying of the cells by lowering the cell water content via cytorrhysis, which is a non-lethal mechanism that does not cause the cell membrane to separate from the cell wall as occurs in plasmolysis. A lower water content will in turn lowers the freezing point of the cytoplasm. The disclosed compositions can comprise from about 0.001% to about 20% by weight, of one or more extracellular desiccants. However, different embodiments of the compositions, for example, compositions adjusted for local conditions, species of plants, frequency of application, and the like, can contain varying amounts of one or more extracellular desiccants.

In one embodiment, the compositions can comprise from about 0.01% to about 10% by weight, of one or more extracellular desiccants. In a further embodiment, the compositions can comprise from about 0.5% to about 7% by weight, of one or more extracellular desiccants. In another embodiment, the compositions can comprise from about 0.1% to about 7% by weight, of one or more extracellular desiccants. In a yet further embodiment, the compositions can comprise from about 1% to about 6% by weight, of one or more extracellular desiccants. In yet another embodiment, the compositions can comprise from about 2% to about 5% by weight, of one or more extracellular desiccants. In a still further embodiment, the compositions can comprise 0.05% to about 1.5% by weight, of one or more extracellular desiccants. In a still yet further embodiment, the compositions can comprise 0.05% to about 1.0% by weight, of one or more extracellular desiccants. In a yet still further embodiment the compositions can comprise 0.1% to about 2.5% by weight, of one or more extracellular desiccants. Particular non-limiting examples of compositions disclosed herein can comprise one or more extracellular desiccants in an amount of 1%, 1.5%, 2%, 2.5%, 3%, 3.5%, 4%, 4.5%, and 5%, where any value can be an upper or lower endpoint of a range. In addition, any fractional amount of an extracellular desiccant is included in the present disclosure, for example, 2.7%, 3.9%, and 4.2%. It is also understood that each unit between two particular units are also disclosed. For example, if 0.01% and 1.5% are disclosed, then 0.02%, 0.05%, 0.1%, 0.25%, 1.3% and the like are also disclosed.

Polyalkylene glycols are disclosed herein as a suitable extracellular desiccant.

One embodiment of polyalkylene glycols relates to polyethylene glycols having the formula:

$$HO(CH_2CH_2O)_xH$$

wherein the index x represent the average number of ethyleneoxy units in the glycol polymer. The index x can be represented by a whole number or a fraction. For example, a polyethylene glycol having an average molecular weight of 8,000 g/mole (PEG 8000) can be equally represented by the formulae:

$$HO(CH_2CH_2O)_{181}H \text{ or } HO(CH_2CH_2O)_{181.4}H$$

or the polyethylene glycol can be represented by the common short hand notation: PEG 8000. This notation, common to the artisan is used interchangeably throughout the specification to indicate polyethylene glycols and their average molecular weight. The formulator will understand that depending upon the source of the polyethylene glycol, the range of molecular weights found within a particular sample or lot can range over more or less values of x. For example, one source of PEG 8000 can include polymers wherein the value of x can be from about 175 to about 187, whereas another source can report the range of molecular weights such that x can be from about 177 to about 184. In fact, the formulator, depending upon the species of plant that is being afforded cryoprotection, can form an admixture of different polyethylene glycols in varying amounts in a final composition. For example, 2% by weight of the composition comprises PEG 4000 and 2% by weight of the composition comprises PEG 8000 for a total of 4% by weight of extracellular desiccant.

One non-limiting example of suitable extracellular desiccants can include polyethylene glycols having an average molecular weight from about 1200 g/mol to about 20,000 g/mol. A further example of a suitable extracellular desiccant can include the polyethylene glycols having an average molecular weight from about 3,000 g/mol to about 12,000 g/mol. Another example of a suitable extracellular desiccant can include the polyethylene glycols having an average molecular weight from about 4,000 g/mol to about 10,000 g/mol. One non-limiting example of a suitable extracellular desiccant is a polyethylene glycol having an average molecular weigh of about 8,000 g/mol, for example, PEG 8000.

Another example of polyalkylene glycols relates to polypropylene glycols having the formula:

$$HO[CH(CH_3)CH_2O]_xH$$

wherein the index x represent the average number of propyleneoxy units in the glycol polymer. As in the case of ethylene glycols, for propylene glycols the index x can be represented by a whole number or a fraction. For example, a polypropylene glycol having an average molecular weight of 8,000 g/mole (PEG 8000) can be equally represented by the formulae:

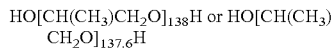

or the polypropylene glycol can be represented by the common, short hand notation: PPG 8000.

One non-limiting example of suitable extracellular desiccants can include polypropylene glycols having an average molecular weight from about 1200 g/mol to about 20,000 g/mol. A further example of a suitable extracellular desiccant can include the polypropylene glycols having an average molecular weight from about 3,000 g/mol to about 12,000 g/mol. Another example of a suitable extracellular desiccant can include the polypropylene glycols having an average molecular weight from about 4,000 g/mol to about 10,000 g/mol. One non-limiting example of a suitable extracellular desiccant is a polypropylene glycol having an average molecular weigh of about 8,000 g/mol, for example, PER 8000.

Polypropylene glycols can be admixed with polyethylene glycols to form a suitable extracellular desiccant for the compositions disclosed herein.

A further example of suitable extracellular desiccants includes poloxamers having the formula:

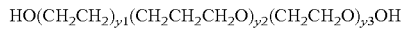

these are nonionic block copolymers composed of a polypropyleneoxy unit flanked by two polyethyleneoxy units. The indices $y^1$, $y^2$, and $y^3$ have values such that the poloxamer has an average molecular weight of from about 1000 g/mol to about 20,000 g/mol. These extracellular desiccants are also well known by the trade name PLURONICS™. These compounds are commonly named with the word Poloxamer followed by a number to indicate the specific co-polymer, for example Poloxamer 407 having two PEG blocks of about 101 units ($y^1$ and $y^3$ each equal to 101) and a polypropylene block of about 56 units. This extracellular desiccant is available from BASF under the trade name LUTROL™ F-17.

However, other extracellular desiccants not specifically described herein are also suitable for use in the disclosed cryoprotectant compositions.

Intracellular Cryoprotectants

The compositions disclosed herein comprise from about 0.001% to about 20% by weight, of one or more intracellular cryoprotectants. Intracellular cryoprotectants can cross the cell membrane by diffusion, and increase the ionic content of both intra- and extracellular compartments, thereby lowering the freezing point and preventing ice crystal formation, much as antifreeze in car radiator lowers the freezing point of the coolant mixture.

However, as with any compound that is absorbed into the cell itself, consideration should be given to several factors. For example, the intracellular cryoprotectant cannot be a compound that itself affects or is a part of the cell's own mechanism for adapting to cold stress and to cold tolerance. A high concentration of a compound, for example, natural cryoprotectants such as sugars and certain alcohols, will also have a role in cell metabolism and catabolism. The presence of excess amounts of these natural plant cryoprotectants can cause allosteric feedback along the biological pathways relating to cryoprotection and my cause damage or resistance to induced natural cryoprotectant.

In one embodiment the compositions can comprise from about 0.1% to about 10% by weight, of one or more intracellular cryoprotectants. In a further embodiment the compositions can comprise from about 0.5% to about 7% by weight, of one or more intracellular cryoprotectants. In another embodiment the compositions can comprise from about 0.1% to about 7% by weight, of one or more intracellular cryoprotectants. In a yet further embodiment the compositions can comprise from about 1% to about 6% by weight, of one or more intracellular cryoprotectants. In yet another embodiment the compositions can comprise from about 2% to about 5% by weight, of one or more intracellular cryoprotectants. In a still further embodiment, the compositions can comprise from about 0.01% to about 1.0% by weight, of one or more intracellular cryoprotectants. In a still further embodiment, the compositions can comprise from about 0.03% to about 0.07% by weight, of one or more intracellular cryoprotectants. In a still another embodiment, the compositions can comprise from about 0.01% to about 1% by weight, of one or more intracellular cryoprotectants. In a yet still further embodiment, the compositions can comprise from about 0.045% to about 0.055% by weight, of one or more intracellular cryoprotectants. In yet another embodiment the compositions can comprise from about 0.02% to about 0.05% by weight, of one or more intracellular cryoprotectants. Particular non-limiting examples of compositions disclosed herein comprise one or more intracellular cryoprotectants in an amount of 1%, 1.5%, 2%, 2.5%, 3%, 3.5%, 4%, 4.5%, and 5%, where any of the stated values can form an upper or lower endpoint of a range. In addition, any fractional amount of an intracellular cryoprotectant is included in the present disclosure, for example, 2.7%, 3.9%, and 4.2%. It is also understood that each unit between two particular units are also disclosed. For example, if 0.01% and 1.5% are disclosed, then 0.02%, 0.05%, 0.1%, 0.25%, 1.3% and the like are also disclosed.

Polyols are disclosed herein as a suitable intracellular cryoprotectant.

One example of polyols suitable for use as an intracellular cryoprotectant is the polyols having the formula:

wherein the index x is from 1 to 20.

In another iteration of polyols the index x is from 1 to 10. In a further iteration the one or more intracellular cryoprotectants are polyols chosen from glycerol, (2R,3R)-butane-1,2,3,4-tetraol, (2S,3R)-butane-1,2,3,4-tetraol, (2R,3S)-butane-1,2,3,4-tetraol, (2S,3S)-butane-1,2,3,4-tetraol, (2R,3R,4R)-pentane-1,2,3,4,5-pentaol, (2S,3R,4R)-pentane-1,2,3,4,5-pentaol, (2R,3S,4R)-pentane-1,2,3,4,5-pentaol, (2R,3R,4S)-pentane-1,2,3,4,5-pentaol, (2S,3S,4R)-pentane-1,2,3,4,5-pentaol, (2S,3R,4S)-pentane-1,2,3,4,5-pentaol, (2R,3S,4S)-pentane-1,2,3,4,5-pentaol, and (2S,3S,4S)-pentane-1,2,3,4,5-pentaol.

In one iteration of the present disclosure, the intracellular cryoprotectant is glycerol. Various polyols are also known by their common names, inter alia, erythritol and xylitol.

In one embodiment the compositions of the present disclosure can comprise from about 0.05% to about 5% of one or more polyols as the intracellular cryoprotectant. In another embodiment the compositions of the present disclosure can comprise from about 0.1% to about 3% of one or more polyols as the intracellular cryoprotectant. In a further embodiment the compositions of the present disclosure can comprise from about 1% to about 5% of one or more polyols as the intracellular cryoprotectant. In one embodiment the compositions of the present disclosure comprises from about 0.1% to about 2% of one or more polyols as the intracellular cryoprotectant.

A non-limiting example of a composition of the present disclosure comprises 0.05% by volume, of one or more polyols. For example 0.046% (w:v) (5 mM) glycerol can be represented as well by 0.05% or by 5 mM. The amount of liquid intracellular cryoprotectant can be expressed either as volume of cryoprotectant per volume of composition, as weight percent of cryoprotectant per volume of composition, or in molarity/molality. For example, the amount of a polyol can be expressed as the number of millimoles of polyol per liter of the final composition. For example, 0.092% (w:v) of glycerol can also be expressed as about 10 mM glycerol, about 0.1%, or about 0.092 g/L.

However, any compound or class of compounds not expressly disclosed herein that is capable of lowering the cell or extracellular water freezing point without inducing plasmolysis is suitable for use as an intracellular or extracellular cryoprotectant in the present disclosure. The use of an intracellular and extracellular cryoprotectant as well as an extracellular desiccant provides the plant to be treated with two levels of cryoprotection.

Surface Active Agents

The compositions disclosed herein comprise one or more surface active agents. The surface active agents disclosed herein assist in uniformly delivering the biologically active agents of the disclosed compositions to the plant cells, either intracellular agents or extracellular agents. The term "surface active agent" includes any surface active ingredient, inter alia, wetting agents, surfactants, and the like. Active agents that are characterized as "wetting agents" can also be characterized by others as "surfactants." The agents of the present disclosure are capable of providing a continuous solution that does not develop phases when the compositions are applied to the plant.

No two plants have identical surface compositions. Even within a subgenus of plants, the variability in plant surface can be dramatic. In addition, some plant cells are covered with a hydrophobic waxy resin, while others are more porous. The compositions disclosed herein are capable of delivering by way of a surface active agent, the combination of active agents further described herein.

The disclosed compositions can comprise from about 0.001% to about 10% by weight, of one or more surface active agents. In another embodiment the disclosed compositions can comprise from about 0.01% to about 5% by weight, of one or more surface active agents. In a further embodiment the disclosed compositions can comprise from about 0.05% to about 2% by weight, of one or more surface active agents. In a yet further embodiment the disclosed compositions can comprise from about 0.05% to about 1% by weight, of one or more surface active agents. In a still further embodiment the disclosed compositions can comprise from about 0.1% to about 1% by weight, of one or more surface active agents. However, different embodiments of the compositions, for example, compositions adjusted for local conditions, species of plants, frequency of application, and the like, can contain varying amounts of one or more surface active agents.

In an embodiment of the compositions disclosed herein, the surface active agent can be a siloxane polymeric material which can be grafted to other surface active units.

One iteration of the disclosure comprises a surface active agent that is a heptamethyl-trisiloxane having the formula:

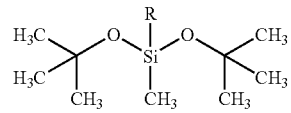

wherein R is a hydrophobic unit comprising ethyleneoxy (EO) units, polypropyleneoxy (PO) units, and mixtures of ethyleneoxy and propyleneoxy units. The molecular weight of the polymer is from about 500 g/mol to about 30,000 g/mole.

One example of a suitable heptamethyl-trisiloxane surface active agent is a comprise an R unit having 100% EO units and an average molecular weight of about 600 g/mol. In this example, the surface active agent can be diluted prior to combination with other ingredients. One source of this polymer is the Setre Chemical Co. or Crompton Corp. which sells this polymer under the trade name SILWET™ L-77 [CAS #27306-78-1]. SILWET™ L-77 can be used in the present composition in an amount from about 0.01% to about 2%. In one series of examples SILWET™ L-77 is present in an amount from about 0.1% to about 1% (v:v).

Another example of a suitable siloxane surfactant includes the polyalkyleneoxy modified trisiloxane comprising 60% EO units and 40% PO units having an average molecular weight of about 600 g/mol. Once source of this polymer is the Comption Corp. which sells this polymer under the name SILWET™ L-7280 [CAS #134180-76-0]. SILWET™ L-7280 can be used in the present composition in an amount from about 0.01% to about 2%. In one series of examples SILWET™ L-7280 is present in an amount from about 0.1% to about 1% (v:v). This surfactant is slightly less hydrophilic and can be admixed with other more hydrophilic surface active agents or can be used alone when the plant surface is such that SILWET™ L-7280 provides optimal performance.

Non-limiting examples of additional siloxane surfactants include SILWET™ L-7608 [CAS #67674-67-3], SILWET™ L-7607 [CAS #117272-76-1], SILWET™ L-8610 [CAS #102783-01-7], SILWET™ L-8620 [CAS #102783-01-7], SILWET™ L-7602 [CAS #68938-54-5], and DBE-712 [CAS #27306-78-1] available from Gelest Inc.

A second embodiment of the surface active agents relates to ethoxylate alcohols having the formula:

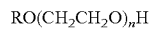

wherein R is a linear or branched alkyl group having from 6 to 20 carbon atoms and n is an integer of about 2 to about 20.

On example of suitable ethoxylate alcohol surfactants are the NEODOL™ ethoxylated alcohols from Shell Chemicals. NEODOL™ 23-1 is a surfactant comprising a mixture of R units that are $C_{12}$ and $C_{13}$ in length with an average of 1 ethoxy unit. Non-limiting examples of ethoxylated alcohols include NEODOL™ 23-1, NEODOL™ 23-2, NEODOL™ 23-6.5, NEODOL™ 25-3, NEODOL™ 25-5, NEODOL™ 25-7, NEODOL™ 25-9, PLURONIC 12R3, and PLURONIC 25R2 available from BASF.

Further examples of surface active agents are those that are amides that are ethoxylate, propoxylated, or mixtures thereof, having the formula:

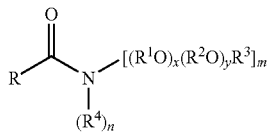

wherein R is $C_7$-$C_{21}$ linear alkyl, $C_7$-$C_{21}$ branched alkyl, $C_7$-$C_{21}$ linear alkenyl, $C_7$-$C_{21}$ branched alkenyl, and mixtures thereof. $R^1$ is ethylene; $R^2$ is $C_3$-$C_4$ linear alkylene, $C_3$-$C_4$ branched alkylene, and mixtures thereof; in some iterations $R^2$ is 1,2-propylene. Nonionic surfactants that comprise a mixture of $R^1$ and $R^2$ units can comprise from about 4 to about 12 ethylene units in combination with from about 1 to about 4 1,2-propylene units. The units can be alternating or grouped together in any combination suitable to the formulator. In one iteration, the ratio of $R^1$ units to $R^2$ units is from about 4:1 to about 8:1. In another iteration, a $R^2$ unit (i.e., 1,2-propylene) is attached to the nitrogen atom followed by the balance of the chain comprising from 4 to 8 ethylene units.

$R^3$ is hydrogen, $C_1$-$C_4$ linear alkyl, $C_3$-$C_4$ branched alkyl, and mixtures thereof; preferably hydrogen or methyl, more preferably hydrogen.

$R^4$ is hydrogen, $C_1$-$C_4$ linear alkyl, $C_3$-$C_4$ branched alkyl, and mixtures thereof. When the index m is equal to 2 the index n must be equal to 0 and the $R^4$ unit is absent and is instead replaced by a —[$(R^1O)_x(R^2O)_yR^3$] unit.

The index m is 1 or 2, the index n is 0 or 1, provided that when m is equal to 1, n is equal to 1; and when m is 2 n is 0; in one example, m is equal to 1 and n is equal to one, resulting in one —[$(R^1O)_x(R^2O)_yR^3$] unit and $R^4$ being present on the nitrogen. The index x is from 0 to about 50, in one embodiment from about 3 to about 25, in another embodiment x is from about 3 to about 10. The index y is from 0 to about 10, in one example y is 0; however, when the index y is not equal to 0, y is from 1 to about 4. In one embodiment all of the alkyleneoxy units are ethyleneoxy units.

In one example, the compositions can comprise from about 0.01% to about 5% by weight, of one or more surface active agents. In a further example, the compositions can comprise from about 0.05% to about 2% by weight, of one or more surface active agents. In another example, the compositions can comprise from about 0.01% to about 1% by weight, of one or more surface active agents. In a yet further embodiment the compositions can comprise from about 0.05% to about 0.5% by weight, of one or more surface active agents. In yet another example, the compositions can comprise from about 0.02% to about 0.5% by weight, of one or more surface active agents. Particular non-limiting examples of compositions disclosed herein comprise one or more surface active agents in an amount of 0.1%, 0.15%, 0.2%, 0.25%, 0.3%, 0.35%, 0.4%, 45%, and 0.5%, where any of the values can be an upper or lower end point of a range.

Anti-Transpirants

The compositions disclosed herein comprise one or more anti-transpirants. The anti-transpirants disclosed herein assist in attenuating moisture loss from plant tissue while being a barrier that is transparent to vapor. The compositions of the present disclosure comprise from about 0.01% to about 10% by weight of one or more anti-transpirants.

The anti-transpirants of the present disclosure form a film or layer over the surface of the plant and protects the plant from excessive moisture loss during exposure to frost or freezing and cold winds. A second benefit is that anti-transpirants retard precipitation-induced wash out of materials assimilated into the leaf tissue, thereby increasing the longevity of foliar spray treatments. There are two primary means for applying anti-transpirants according to the present disclosure. A first method is to apply a monomeric material or other small molecule that once exposed to the surface of the plant will form a film. The second method is to apply a pre-formed polymeric material.

One example of the first method for delivering an anti-transpirant barrier to plants relates to applying a polymerizable monomer or small copolymer that forms a transpiration boundary once applied to the plant surface. One non-limiting example, is to apply a terpenoid monomer or dimer that once exposed to the sunlight and or other outdoor conditions will begin to form a polymeric film or barrier against transpiration. One example is to apply a dimer of β-pinene, di-1-menthene, a Lewis acid catalyzed dimer product of the naturally occurring terpene. This dimer, when sprayed onto the surface of a plant, will begin to polymerize thereby forming longer chains. One advantage of films or barriers of this type is that only the surface layer of the film undergoes any significant polymerization. Terpenes of this type will typically become a solid, flaky powder that subsequently weathers away without any lasting effects to the plant itself. One source of the terpene dimer, di-1-menthene, is sold as WILT-PRUF™ by Wilt-Pruf Products, Inc. Essex, Conn. This product when used as an anti-transpirant component according to the present disclosure can be pre-diluted in water before combination with other actives.

An example of the second method for forming an anti-transpiration barrier is to apply a pre-formed barrier material, for example, a polymer or mixture of polymers that form a barrier against excessive transpiration once the carrier has evaporated.

A first embodiment of this means for forming an anti-transpiration barrier relates to homopolymers or co-polymers that are formed from one or more "vinyl monomers" having the formula:

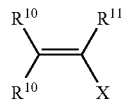

wherein each $R^{10}$ is independently hydrogen, $C_1$-$C_{12}$ alkyl, $C_1$-$C_{12}$ alkoxy, phenyl, substituted phenyl, benzyl, substituted benzyl, carbocyclic, heterocyclic, and mixtures thereof; $R^{11}$ is hydrogen, halogen, preferably chlorine or fluorine, $C_1$-$C_{12}$ alkyl, $C_1$-$C_{12}$ alkoxy, phenyl, substituted phenyl, benzyl, substituted benzyl, carbocyclic, heterocyclic, and mixtures thereof; X is hydrogen, hydroxyl, halogen, —$(CH_2)_m CH_2OH$, —$(CH_2)_m COR$, —$(CH_2)_m CH_2 OCOR'$ wherein R is OR', —$N(R')_2$, —$(CH_2)_n N(R'')_2$, and mixtures thereof; each R' is independently hydrogen, $C_1$-$C_8$ alkyl, $C_2$-$C_8$ hydroxyalkyl, —$(CH_2)_n N(R'')_2$, and mixtures thereof; wherein R" is independently hydrogen, $C_1$-$C_4$ alkyl, and mixtures thereof; the index m is from 0 to 6, the index n is from 2 to 6. Non-limiting examples of preferred vinyl monomers include, ethylene, propylene, butylene, styrene, vinyl alcohol, crotyl alcohol, acrylic acid, styrylacetic acid, methacrylic acid, crotonic acid, 3,3-dimethyl-acrylic acid, methyl acrylate, ethyl acrylate, n-propyl acrylate, isopropyl acrylate, butyl acrylate, methyl methacrylate, ethyl methacrylate, n-propyl methacrylate, isopropyl methacrylate, butyl methacrylate, methyl 3,3-dimethyl-acrylate, ethyl 3,3-dimethyl-acrylate, n-propyl 3,3-dimethyl-acrylate, isopropyl 3,3-dimethyl-acrylate, butyl 3,3-dimethyl-acrylate, acrylamide, N-methyl acrylamide, N,N-dimethyl acrylamide, N-(aminoethyl)methyl acrylamide, vinyl acetate, and mixtures thereof.

Another example comprises polymers that provide for a specific range of vapor transfer rates from a plant surface. One example is a polymer that provides a vapor transfer rate of less than about 10 g-mm/m$^g$-day, while other examples provide a rate of about 5 g-mm/m$^2$-day. However, formulators can restrict the water vapor transfer rate to about 2 g-mm/m$^2$-day in preparing other suitable examples. Suitable means for determining water vapor transmission rates of polymers is by ASTM D1653 for a 0.02 inch (20 mm) film, ASTM E-96-66, Procedure E at 90% relative humidity and 100° F. (37.78° C.) for a 1 mm or 2 mm film, or TAPPI T 464 os-79 for a 2 mm film.

In addition, the anti-transpirants used for the present disclosure in a first embodiment have a glass transition temperature, $T_g$, greater than about minus 30° C. The glass transition temperature, $T_g$, of a particular co-polymer can be approximated beforehand by the Fox formula (Fox, *Bull. Am. Phys. Soc.* 1:123 (1956), included herein by reference):

$$\frac{1}{T_{Co}} = \frac{W_1}{T_1} + \frac{W_2}{T_2} + \ldots \frac{W_n}{T_n}$$

wherein $W_1$ represents the weight portion of monomer 1, $W_2$ represents the weight portion of monomer 2, $T_1$ the glass transition temperature of the polymerized monomer 1 in degrees Kelvin, K, $T_2$ the glass transition temperature of the polymerized monomer 2 in K, $T_{Co}$, the glass transition temperature of the copolymer in K.

In one example, the compositions of the present disclosure can comprise from about 0.05% to about 5% of one or more anti-transpirants. In another example, the compositions of the present disclosure can comprise from about 0.1% to about 3% of one or more anti-transpirants. In a further example, the compositions of the present disclosure can comprise from about 1% to about 5% of one or more anti-transpirants. In one example, the compositions of the present disclosure can comprise from about 0.1% to about 2% of one or more anti-transpirants.

Non-limiting examples of suitable copolymers comprises the reaction product obtained when polymerizing:
  i) from about 20% to about 60% by weight, of methyl methacrylate;
  ii) from about 20% to about 60% by weight, of butyl acrylate; and
  iii) from about 0.5% to about 20% by weight, of acrylic acid.

Another copolymer comprises the reaction product obtained when reacting:
  i) from about 40% to about 50% by weight, of methyl methacrylate;
  ii) from about 40% to about 50% by weight, of butyl acrylate; and
  iii) from about 5% to about 15% by weight, of acrylic acid.

A further example of a copolymer suitable for use in compositions of the present disclosure comprises:
  i) about 43% by weight, of methyl methacrylate;
  ii) about 47% by weight, of butyl acrylate; and
  iii) about 10% by weight, of acrylic acid.

In each of the above examples, neutralization of the acrylic acid residues can be achieved with a suitable base, for example, at least 5%, or in another case 10% of the acrylic acid residues.

Silicate

The composition of the present disclosure comprise from about 0.01% to about 5% of one or more sources of water-soluble silicate. In one embodiment the compositions of the present disclosure comprises from about 0.05% to about 5% of one or more sources of water-soluble silicate. In another embodiment the compositions of the present disclosure comprises from about 0.1% to about 3% of one or more sources of water-soluble silicate. In a further embodiment the compositions of the present disclosure comprises from about 1% to about 5% of one or more sources of water-soluble silicate. In one embodiment the compositions of the present disclosure comprises from about 0.1% to about 2% of one or more sources of water-soluble silicate. The silicate can have any suitable cation, inter alia, potassium, sodium, lithium, calcium, ammonium, and the like.

The first embodiment relates to compositions comprising potassium silicate. Although potassium silicate is water soluble, depending upon the concentration and use thereof, other admixture can be advantageous. For example, one commercial source of potassium silicate is AGSIL™ 25F, which is a white solid of approximately one inch flakes that are soluble in water. AGSIL™ 25F comprises 71.0% SiO$_2$ and 28.4% K$_2$O. However, a more convenient source of potassium silicate that can be readily diluted of use in the presently disclosed composition is AGSIL™ 25, which is a solution comprising 29.1% of the potassium salt of silicic acid (20.8% SiO$_2$ and 8.3% K$_2$O) and 70.9% water.

In one example, described herein below 0.5% of the exemplified composition comprises AGSIL™ 25 on a volume to volume basis.

Carriers

The compositions disclosed herein comprise one or more carriers. One embodiment comprises water as the carrier. In another embodiment the carrier comprises water and a co-solvent. The co-solvent can be an alcohol, inter alia, methanol, ethanol, or the like or the co-solvent can be one or more plasticizers utilized in forming or dispersing the anti-transpirant.

Exemplary Compositions

The following are non-limiting examples of some specific compositions according to the present disclosure:

TABLE 1

| Component | 1 | 2 | 3 | 4 | 5 |
|---|---|---|---|---|---|
| PEG MW = 8000 | 4% | — | — | 3% | 3% |
| PEG MW = 6500 | — | 4% | — | — | — |
| PEG MW = 4000 | — | — | 4% | — | 1% |
| glycerol | 0.4% | 0.5% | 0.5% | 0.5% | 1.0% |
| AG SIL 25 | 0.5% | 0.5% | 0.5% | 0.5% | 0.5% |
| SILWET L-77 ™ | 0.1% | 0.1% | 0.1% | 0.1% | 0.1% |
| WILT-PRUF ™ | 2% | 2% | 2% | 2% | 2% |
| Water* | balance | balance | balance | balance | balance |

*In one convenient procedure, commercially available WILT-PRUF ™ is diluted 1/50 with water and the balance of ingredients is then added to this solution.

TABLE 2

| Component | 6 | 7 | 8 | 9 | 10 |
|---|---|---|---|---|---|
| PEG MW = 8000 | 8% | 4% | 2% | 1% | 0.8% |
| glycerol | 0.5% | 0.5% | 0.5% | 0.5% | 0.5% |
| AG SIL 25 | 0.5% | 0.5% | 0.5% | 0.5% | 0.5% |
| SILWET L-77 ™ | 0.1% | 0.1% | 0.1% | 0.1% | 0.1% |
| WILT-PRUF ™ | 2% | 2% | 2% | 2% | 2% |
| Water | balance | balance | balance | balance | balance |

TABLE 3

| Component | 11 | 12 | 13 | 14 | 15 |
|---|---|---|---|---|---|
| PEG MW = 8000 | 4% | 4% | 4% | 4% | — |
| PEG MW = 4000 | — | — | — | — | 5% |
| glycerol | 0.2% | — | — | — | — |
| 2,2'-oxydiethanol | 0.3% | 0.5% | — | — | — |
| erythritol | — | — | 0.5% | — | 0.2% |
| xylitol | — | — | — | 0.5% | — |
| AG SIL 25 | 0.5% | 0.5% | 0.5% | 0.5% | 0.5% |
| SILWET L-77 ™ | 0.1% | 0.1% | 0.1% | 0.1% | 0.1% |
| WILT-PRUF ™ | 2% | 2% | 2% | 2% | 2% |
| Water | balance | balance | balance | balance | balance |

TABLE 4

| Component | 16 | 17 | 18 | 19 | 20 |
|---|---|---|---|---|---|
| PEG MW = 8000 | 4% | 4% | 4% | 4% | 4% |
| glycerol | 0.5% | 0.5% | 0.5% | 0.5% | 0.5% |
| AG SIL 25 | 0.1% | 0.2% | 0.25% | 0.3% | 0.4% |
| SILWET L-77 ™ | 0.1% | 0.1% | 0.1% | 0.1% | 0.1% |
| WILT-PRUF ™ | 2% | 2% | 2% | 2% | 2% |
| Water* | balance | balance | balance | balance | balance |

*In one convenient procedure, commercially available WILT-PRUF ™ is diluted 1/50 with water and the balance of ingredients is then added to this solution.

TABLE 5

| Component | 21 | 22 | 23 | 24 | 25 |
|---|---|---|---|---|---|
| PEG MW = 8000 | 4% | 4% | 4% | 4% | 4% |
| glycerol | 0.5% | 0.5% | 0.5% | 0.5% | 0.5% |
| AG SIL 25 | 0.1% | 0.1% | 0.1% | 0.1% | 0.1% |
| SILWET L-77 ™ | 0.05% | 0.15% | 0.2% | 0.25% | 0.3% |
| WILT-PRUF ™ | 2% | 2% | 2% | 2% | 2% |
| Water* | balance | balance | balance | balance | balance |

*In one convenient procedure, commercially available WILT-PRUF ™ is diluted 1/50 with water and the balance of ingredients is then added to this solution.

TABLE 6

| Component | 26 | 27 | 28 | 29 | 30 |
|---|---|---|---|---|---|
| PEG MW = 8000 | 4% | 4% | 4% | 4% | 4% |
| glycerol | 0.5% | 0.5% | 0.5% | 0.5% | 0.5% |
| AG SIL 25 | 0.1% | 0.1% | 0.1% | 0.1% | 0.1% |
| SILWET L-77 ™ | 0.1% | 0.1% | 0.1% | 0.1% | 0.1% |
| WILT-PRUF ™ | 0.5% | 1% | 1.5% | 2.5% | 4% |
| Water | balance | balance | balance | balance | balance |

TABLE 7

| Component | 31 | 32 | 33 | 34 | 35 |
|---|---|---|---|---|---|
| PEG MW = 8000 | 4% | — | — | — | — |
| PEG MW = 7000 | — | 4% | — | — | — |
| PEG MW = 6000 | — | — | 4% | — | — |
| PEG MW = 5000 | — | — | — | 4% | — |
| PEG MW = 4000 | — | — | — | — | 4% |
| glycerol | 1.5% | 0.5% | 0.5% | 0.5% | 0.5% |
| AG SIL 25 | 0.1% | 0.1% | 0.1% | 0.1% | 0.1% |
| SILWET L-77 ™ | 0.1% | 0.1% | 0.1% | 0.1% | 0.1% |
| WILT-PRUF ™ | 2% | 2% | 2% | 2% | 2.5% |
| Water* | balance | balance | balance | balance | balance |

*In one convenient procedure, commercially available WILT-PRUF ™ is diluted 1/50 with water and the balance of ingredients is then added to this solution.

TABLE 8

| Component | 36 | 37 | 38 | 39 | 40 |
|---|---|---|---|---|---|
| PEG MW = 8000 | 4% | — | — | 3% | 3% |
| PEG MW = 6500 | — | 4% | — | — | — |
| PEG MW = 4000 | — | — | 4% | — | 1% |
| glycerol | 0.04% | 0.05% | 0.05% | 0.05% | 0.1% |
| AG SIL 25 | 0.5% | 0.5% | 0.5% | 0.5% | 0.5% |
| SILWET L-77 ™ | 0.1% | 0.1% | 0.1% | 0.1% | 0.1% |
| WILT-PRUF ™ | 2% | 2% | 2% | 2% | 2% |
| Water | balance | balance | balance | balance | balance |

TABLE 9

| Component | 41 | 42 | 43 | 44 | 45 |
|---|---|---|---|---|---|
| PEG MW = 8000 | 8% | 4% | 2% | 1% | 0.8% |
| glycerol | 0.05% | 0.05% | 0.05% | 0.05% | 0.05% |
| AG SIL 25 | 0.5% | 0.5% | 0.5% | 0.5% | 0.5% |
| SILWET L-77 ™ | 0.1% | 0.1% | 0.1% | 0.1% | 0.1% |
| WILT-PRUF ™ | 2% | 2% | 2% | 2% | 2% |
| Water | balance | balance | balance | balance | balance |

TABLE 10

| Component | 46 | 47 | 48 | 49 | 50 |
|---|---|---|---|---|---|
| PEG MW = 8000 | 4% | 4% | 4% | 4% | — |
| PEG MW = 4000 | — | — | — | — | 5% |
| glycerol | 0.02% | — | — | — | — |
| 2,2'-oxydiethanol | 0.03% | 0.05% | — | — | — |
| erythritol | — | — | 0.05% | — | 0.02% |
| xylitol | — | — | — | 0.05% | — |
| AG SIL 25 | 0.5% | 0.5% | 0.5% | 0.5% | 0.5% |
| SILWET L-77 ™ | 0.1% | 0.1% | 0.1% | 0.1% | 0.1% |
| WILT-PRUF ™ | 2% | 2% | 2% | 2% | 2% |
| Water* | balance | balance | balance | balance | balance |

*In one convenient procedure, commercially available WILT-PRUF ™ is diluted 1/50 with water and the balance of ingredients is then added to this solution.

TABLE 11

| Component | 51 | 52 | 53 | 54 | 55 |
|---|---|---|---|---|---|
| PEG MW = 8000 | 4% | 4% | 4% | 4% | 4% |
| glycerol | 0.05% | 0.05% | 0.05% | 0.05% | 0.05% |
| AG SIL 25 | 0.1% | 0.2% | 0.25% | 0.3% | 0.4% |
| SILWET L-77 ™ | 0.1% | 0.1% | 0.1% | 0.1% | 0.1% |
| WILT-PRUF ™ | 2% | 2% | 2% | 2% | 2% |
| Water* | balance | balance | balance | balance | balance |

*In one convenient procedure, commercially available WILT-PRUF ™ is diluted 1/50 with water and the balance of ingredients is then added to this solution.

TABLE 12

| Component | 56 | 57 | 58 | 59 | 60 |
|---|---|---|---|---|---|
| PEG MW = 8000 | 4% | 4% | 4% | 4% | 4% |
| glycerol | 0.05% | 0.05% | 0.05% | 0.05% | 0.05% |
| AG SIL 25 | 0.1% | 0.1% | 0.1% | 0.1% | 0.1% |
| SILWET L-77 ™ | 0.05% | 0.15% | 0.2% | 0.25% | 0.3% |
| WILT-PRUF ™ | 2% | 2% | 2% | 2% | 2% |
| Water | balance | balance | balance | balance | balance |

TABLE 13

| Component | 61 | 62 | 63 | 64 | 65 |
|---|---|---|---|---|---|
| PEG MW = 8000 | 4% | 4% | 4% | 4% | 4% |
| glycerol | 0.05% | 0.05% | 0.05% | 0.05% | 0.05% |

TABLE 13-continued

| Component | 61 | 62 | 63 | 64 | 65 |
|---|---|---|---|---|---|
| AG SIL 25 | 0.1% | 0.1% | 0.1% | 0.1% | 0.1% |
| SILWET L-77 ™ | 0.1% | 0.1% | 0.1% | 0.1% | 0.1% |
| WILT-PRUF ™ | 0.5% | 1% | 1.5% | 2.5% | 4% |
| Water | balance | balance | balance | balance | balance |

TABLE 14

| Component | 66 | 67 | 68 | 69 | 70 |
|---|---|---|---|---|---|
| PEG MW = 8000 | 4% | — | — | — | — |
| PEG MW = 7000 | — | 4% | — | — | — |
| PEG MW = 6000 | — | — | 4% | — | — |
| PEG MW = 5000 | — | — | — | 4% | — |
| PEG MW = 4000 | — | — | — | — | 4% |
| glycerol | 0.15% | 0.05% | 0.05% | 0.05% | 0.05% |
| AG SIL 25 | 0.1% | 0.1% | 0.1% | 0.1% | 0.1% |
| SILWET L-77 ™ | 0.1% | 0.1% | 0.1% | 0.1% | 0.1% |
| WILT-PRUF ™ | 2% | 2% | 2% | 2% | 2.5% |
| Water | balance | balance | balance | balance | balance |

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present disclosure which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

The following are non-limiting examples of a procedure for preparing the disclosed compositions.

Example 71

To a 2 L beaker equipped with a TEFLON™ paddled stirrer is charged water (ca. 500 mL) and the commercially available di-terpene anti-transpirant WILT-PRUF™ (20 g) is added. SILWET™ L-77 (1 g) is added to the solution using the difference in weight of the stock container of the surface active agent to determine the amount added. AGSIL™ 25F (5 g) is added and the solution stirred for 5 minutes. PEG 8000 (40 g) is then metered into the solution over about 5 minutes. Glycerol (5 g) is then added and the solution stirred an additional one minute. Water is then added up to a total volume of 1000 mL and the mixture is stirred an additional 5 minutes. At this point the composition is ready to use, and remains stable indefinitely at room temperature.

Example 72

To a 2 L beaker equipped with a TEFLON™ paddled stirrer is charged water (ca. 500 mL) and the commercially available di-terpene anti-transpirant WILT-PRUF™ (20 g) is added. SILWET™ L-77 (1 g) is added to the solution using the difference in weight of the stock container of the surface active agent to determine the amount added. AGSIL™ 25F (5 g) is added and the solution stirred for 5 minutes. PEG 8000 (40 g) is then metered into the solution over about 5 minutes. Glycerol (0.5 g) is then added and the solution stirred an additional one minute. Water is then added up to a total volume of 1000 mL and the mixture is stirred an additional 5 minutes. At this point the composition is ready to use, and remains stable indefinitely at room temperature.

Example 73

To a 2 L beaker equipped with a TEFLON™ paddled stirrer is charged water (ca. 500 mL) and the commercially available di-terpene anti-transpirant WILT-PRUF™ (20 g) is added. SILWET™ L-77 (1 g) is added to the solution using the difference in weight of the stock container of the surface active agent to determine the amount added. AGSIL™ 25F (5 g) is added and the solution stirred for 5 minutes. An admixture of PEG 8000 (20 g) and PEG 4000 (20 g) is then metered into the solution over about 5 minutes. Glycerol (0.5 g) is then added and the solution stirred an additional one minute. Water is then added up to a total volume of 1000 mL and the mixture is stirred an additional 5 minutes. At this point the composition is ready to use, and remains stable indefinitely at room temperature.

Example 74

To a 2 L beaker equipped with a TEFLON™ paddled stirrer is charged water (ca. 500 mL) and the commercially available di-terpene anti-transpirant WILT-PRUF™ (20 g) is added. SILWET™ L-77 (1 g) is added to the solution using the difference in weight of the stock container of the surface active agent to determine the amount added. AGSIL™ 25F (5 g) is added and the solution stirred for 5 minutes. An admixture of PEG 8000 (30 g) and PEG 4000 (10 g) is then metered into the solution over about 5 minutes. Glycerol (0.5 g) is then added and the solution stirred an additional one minute. Water is then added up to a total volume of 1000 mL and the mixture is stirred an additional 5 minutes. At this point the composition is ready to use, and remains stable indefinitely at room temperature.

Procedures

Prior to Field Test Experiments, specimen testing was conducted on freshly-excised plant leaves, using temperatures of from minus 3° C. to minus 14.9° C. designed to cause near-complete to complete destruction of specimens. The purpose of these experiments was to document the most effective spray composition for various plant species. Controls were treated with tap water while treated specimens were sprayed with one or more of the disclosed compositions. Once sprayed, leaves were allowed to air dry for about 30 minutes before being placed in environmental chambers for a period of 30 to 60 minutes at a test temperature. The chambers (Revco) were temperature calibrated prior to and during experiments with electronic thermometers. Opening the chamber to insert samples caused the air temperature within to rise, and it generally took about 5-15 minutes for temperatures to cool back down to the pre-set test temperature. Tissue cooling rates were from about 0.5° C./min. to about 1° C./min. This rate is much faster than those typically seen in the field experiment where temperatures tend to fall at a rate of from about 1° C./hour to about 2° C./hour. After incubation at the test temperature, chambers are turned off, and excised leaves are allowed to warm gradually over a period of about 10 to 30 minutes until they are close to the ambient laboratory temperature. Leaves are then placed in clear polyethylene bags with moisture seals and incubated for at least 24 hours at room temperature before visual scoring for cold-necrotic tissue using the areal % viable leaf tissue remaining index method described by Francko, D. A. et al., 2002. Cold-hardy palms in Southwestern Ohio Winter damage, mortality and recovery. *Palms* 46(1):5-13. This procedure is outlined herein below.

Damage assessments of each individual specimen are assigned a numerical ranking of foliar damage by evaluating and scoring each specimen on the basis of leaf foliage killed (visual observation of the areal extent of brown and/or necrotic tissue) versus the total foliar area. The data are then grouped into broad numerical rankings: 1=essentially no foliar damage, 2=15% or less leaf tissue area killed, 3=15 to 30% killed, 4=30 to 75% killed, 5=75 to 90% killed, 6=greater than 90% leaf destruction, but petiole bases green, and 7=all above ground tissue killed. Numerical scores for each plant are then interpolated to the nearest 0.5 unit. Data for all specimens are pooled by species and mean damage estimates computed as a function of temperature.

Results for the following non-limiting examples of species are provided. These species were tested with compositions according to the present disclosure and evaluated for their resistance to frost/freeze conditions: *Trachycarpus fortunei*, *Sabal palmetto*, *Citrus sinensis*, *Musa basjoo*, *Musa acuminata*, *Spathiphyllum* sp., and *Chamaedorea cataractarum*.

Example 75

Prior to Field Test Experiments, specimen testing was conducted on freshly-excised plant leaves, using temperatures of from minus 3° C. to minus 14.9° C. designed to cause near-complete to complete destruction of specimens. Controls were treated with tap water while treated specimens were sprayed with one or more of the disclosed compositions. Once sprayed, leaves were allowed to air dry for about 30 to 60 minutes before being placed in environmental chambers for a period of 30 minutes at a test temperature. The chambers (Revco) were temperature calibrated prior to and during experiments with electronic thermometers. Opening the chamber to insert samples caused the air temperature within to rise, and it generally took about 5 to 15 minutes for temperatures to cool back down to the pre-set test temperature. Tissue cooling rates were from about 0.5° C./min. to about 1° C./min. This rate is much faster than those typically seen in the field experiment where temperatures tend to fall at a rate of from about 1° C./hour to about 2° C./hour. After incubation at the test temperature, chambers are turned off, and excised leaves are allowed to warm gradually over a period of about 10 to 30 minutes until they are close to the ambient laboratory temperature. Leaves are then placed in clear polyethylene bags with moisture seals and incubated for at least 24 hours at room temperature before visual scoring for cold-necrotic tissue using the areal % viable leaf tissue remaining index method described by Francko et al., 2002. Cold-hardy palms in Southwestern Ohio: Winter damage, mortality and recovery. *Palms* 46(1):5-13, included herein by reference. This procedure is outlined herein below.

Damage assessments of each individual specimen are assigned a numerical ranking of foliar damage by evaluating and scoring each specimen on the basis of leaf foliage killed (visual observation of the areal extent of brown and/or necrotic tissue) versus the total foliar area. The data are then grouped into broad numerical rankings: 1=essentially no foliar damage, 2=15% or less leaf tissue area killed, 3=15 to 30% killed, 4=30 to 75% killed, 5=75 to 90% killed, 6=greater than 90% leaf destruction, but petiole bases green, and 7=all above ground tissue killed. Numerical scores for each plant are then interpolated to the nearest 0.5 unit. Data for all specimens are pooled by species and mean damage estimates computed as a function of temperature.

Results for the following non-limiting examples of species are provided. These species were tested with compositions according to the present disclosure and evaluated for their resistance to frost/freeze conditions: *Trachycarpus fortunei*, *Sabal palmetto*, *Citrus sinensis*, *Musa basjoo*, *Musa acuminata*, *Spathiphyllum* sp., and *Chamaedorea cataractarum*.

*Trachycarpus fortunei*, also known as Windmill palm or Chinese windmill palm, is the palm that can be cultivated the farthest north of any arborescent palm species and therefore has high economical value. This plant is cultivated in the British Isles, Northern Europe (e.g., Germany, the Netherlands, Belgium, and Denmark), the northwestern coast of the United States and British Columbia.

*Sabal palmetto*, also known as the cabbage palm, is the state tree of Florida and South Carolina. This palm is found throughout the coastal southeastern United States and is resistant to salt air. However, businesses, restaurants, hotels, and private gardeners have begun to use this palm as a decorative plant in more northern areas, and reproductively-active specimens are now found as far north as Tennessee.

*Chamaedorea cataractarum*, as known as cat palm, is a subtropical palm species cultivated outdoors through Zone 9 and used in colder areas as a potted specimen. It is one of the most common house plant selections in cold winter areas.

Chinese windmill palm, cabbage palm, and cat palm leaves were treated with various solutions disclosed in Table 2 herein above. The results of these tests are summarized herein below in Table 15.

TABLE 15

*Trachycarpus* and *S. palmetto* treated at minus 14.9° C. for 1 hour, and *C. cataractarum* at minus 5.6° C. for 1 hour.

| | Foliar Damage Index | | |
| --- | --- | --- | --- |
| Treatment | *Trachycarpus* | *S. palmetto* | *C. cataractarum* |
| Control | 7.0 | 7.0 | 7.0 |
| Table 9, #45 | 4.0 | 4.0 | — |
| Table 9, #43 | 2.0 | 3.5 | 2.0 |
| Table 9, #42 | 3.5 | 4.0 | 4.0 |

Although the FDI is a valuable tool for assessing the degree of cold damage in plant foliage, it does not fully address the real-world concerns of horticulturists, agriculture, and individual home gardeners. Specifically, it is important to know the critical environmental temperatures for two important foliar variables: the temperature at which foliage begins to be damaged by cold and the warmest temperature that causes complete foliar mortality. In assigning USDA Zone ratings to various plants, horticulturists take these critical temperatures into account. For example, a subtropical plant (e.g., peace lily) that is rated as marginally hardy in Zone 9 (average annual minimum temperature minus 1.2° C. to minus 6.6° C.) will start showing foliar damage near the warmest part of the Zone temperature range and be heavily damaged (and perhaps killed) by temperatures at the coldest end of the annual Zone range.

As noted earlier, many agricultural and horticultural plants are currently being grown at the margins of (and frequently slightly beyond) their nominal USDA Zone ratings. Thus, there is great interest in strategies that lower these critical temperatures and thereby 'extend' the Zone rating for popular ornamentals and crop plants. If, for example, a strategy resulted in a decrease of 3° C. in the critical temperatures for first foliar damage and foliar mortality in peace lily, the effect would be to increase the Zone rating for that plant by the equivalent of more than ½ of a full USDA Zone—making it fully hardy in Zone 9 and marginally hardy in the warmer regions of Zone 8.

A linear regression modeling method was used to determine the Foliar Damage Threshold (FDT; the coldest temperature at which 0% foliar damage occurs after 30 min exposure) and the Foliar Mortality Threshold (FMT; the warmest temperature at which 100% foliar mortality occurs after 30 min exposure) for a non-limiting groups of plants.

Plants included cabbage palm, windmill palm, cat palm, peace lily, *Syngonium* species, sweet orange, Japanese fiber banana, and *M. acuminata*. This same methodology was used to compute the temperature at which selected flowers (sweet orange and miniature rose) suffer complete mortality.

Leaves were excised and sprayed either with tap water (controls) or various solutions from Table 13. After 30 min drying, leaves were incubated in environmental chambers for 30 min at various temperatures as described earlier. The temperatures used spanned a range from well above the suspected FDT to well below the expected FMT. After incubation, the leaves were removed from chambers, processed as described earlier, and a visual estimate was made of the areal percentage of viable leaf tissue remaining after each cold treatment. An example of this approach and the resulting data set for peace lily treated with solution 42 from Table 9 is disclosed herein in Table 16.

TABLE 16

| Temp ° C. | control | treated |
|---|---|---|
| −1.0 | 100 | — |
| −1.4 | 97 | — |

TABLE 16-continued

| Temp ° C. | control | treated |
|---|---|---|
| −2.3 | 65 | — |
| −3.0 | 5 | — |
| −6.4 | 0 | 98 |
| −6.6 | — | 100 |
| −6.9 | — | 29 |
| −7.0 | — | 10 |
| −7.1 | — | 10 |
| −7.5 | — | 0 |

Rather than grouping these into broad numerical categories (as with FDI determinations earlier) the percentage viable tissue remaining values were graphically plotted as a dependent function of the incubation temperature. Linear regression analysis was then performed on these data sets for each species above, permitting the direct determination of both the FDT (the Y-intercept of the regression line) and the FMT (the X-intercept of the regression line). For all species examined and for both controls and treated leaves, there was a significant ($r^2$ values ranging from 0.59 to 0.99, all significant at the 5% level or better) direct linear relationship between decreasing temperature and the degree of foliar damage. By analyzing the differences in X- and Y-intercepts between control and treated leaves, it was then possible to compute FDT and FMT values for both controls and treated leaves, and also to compute a delta value for both FDT and FMT as a result of Table 2 spray treatments. These data are disclosed herein in Table 17 below.

TABLE 17

Foliar Damage Threshold (FDT) and Foliar Mortality Threshold (FMT) for various plants, with and without spray treatment, based on linear regression modeling ($r^2$ values 0.59 to 0.99; all significant at $P < 0.05$) and Mortality Threshold for fully expanded flowers.

| Species | Table 9 sol. | Damage Threshold ° C. | | | Mortality Threshold ° C. | | |
|---|---|---|---|---|---|---|---|
| | | control | treated | ΔFDT | control | treated | ΔFMT |
| FOLIAGE | | | | | | | |
| S. palmetto | 43 | −9.6 | −12.4 | −2.8 | −15.1 | −17.8 | −2.7 |
| T. fortunei | 43 | −12.0 | −14.0 | −2.0 | −15.7 | −19.2 | −3.5 |
| C. cataractarum | 43 | −1.0 | −4.4 | −3.4 | −4.3 | −7.6 | −3.3 |
| Spathiphyllum | 42 | −1.1 | −6.3 | −5.2 | −3.3 | −7.3 | −4.0 |
| Syngonium | 42 | −1.2 | −4.7 | −3.5 | −3.2 | −8.4 | −5.2 |
| C. sinensis | 44 | −5.0 | −6.3 | −1.3 | −7.3 | −8.7 | −1.4 |
| M. basjoo | 42 | −0.5 | −4.2 | −3.7 | −9.6 | −12.8 | −3.2 |
| M. acuminata | 42 | −0.8 | −3.0 | −2.2 | −3.2 | −7.3 | −4.1 |
| FLOWERS | | | | | | | |
| C. sinensis | 44 | — | — | — | −1.2 | −2.4 | −1.2 |
| Rosa miniature | 44 | — | — | — | −4.5 | −5.7 | −1.2 |

For all plant species tested, treatment with Table 9 solutions greatly lowered both the FDT and the FMT over controls. In general, the greatest effects were noted in high-water-content, herbaceous subtropical ornamentals (peace lily, *Syngonium*, bananas) with control FDT values only slightly below freezing. In these plants, delta FDT values ranged from minus 2.2° C. to minus 5.2° C., the equivalent of 0.40 to 0.94 USDA Zone equivalents, with a mean ΔFDT of minus 3.7° C. (0.67 Zone equivalents). Palm ΔFDT values ranged from minus 2.0° C. in very cold-tolerant windmill palm to minus 3.4° C. in the subtropical cat palm, the equivalent of 0.36 to 0.61 USDA Zone equivalents, with a mean of 0.49 USDA Zone equivalents for the three species. *C. sinensis* (sweet orange) had the lowest ΔFDT value (−1.3° C.) of the non-limiting group of plants tested, but even this modest value translates to 0.23 USDA Zone equivalents. The magnitude of ΔFDT values for Table 9-treated plant leaves paralleled those for FDT determinations, ranging from minus 3.2° to minus 5.2° C. (mean minus 4.1° C. or 0.74 USDA Zone equivalents) in herbaceous subtropicals, minus 2.7° C. to minus 3.5° C. (mean minus 3.2° C. or 0.58 USDA Zone equivalents) in palms, and minus 1.4° C. in sweet orange (0.25 USDA Zone equivalents).

FIG. 1 graphically represents the decrease in the Foliar Mortality Threshold for *Spathiphyllum* sp. at various temperatures after treatment with a composition No. 42 of Table 9 as disclosed herein. The linear relationship between exposure temperature and the percentage of live leaf tissue remaining after 24 hours in whole excised leaves of *Spathiphyllum* sp. (peace lily) shows that the Foliar Damage Threshold does not begin until the exposure is at a temperature below the Foliar Mortality Threshold of untreated plants.

Taken together, the data disclosed in Table 17 indicates the efficacy of the disclosed compositions. In tender plants normally damaged by frost and killed by hard freezes, the disclosed compositions increase cold tolerance by the equivalent of ca. ½ to nearly 1 full USDA Zone equivalent. This has the effect of extending the growing season for tender vegetation in colder areas and provides a method for eliminating the possibility of major damage in warmer-winter areas. In addition, the disclosed compositions effectively lower the FDT and FMT temperatures for plants, such as cold-hardy palms, that are already endowed with significant cold-tolerance capability, adding the equivalent of more that ½ of a USDA Zone equivalent to damage and mortality critical temperatures. Put another way, this means that a cabbage palm, currently marginally hardy in Atlanta, Ga. can be grown without major damage or complete foliar mortality in that city and can now be found to be hardy as far north as Knoxville or Nashville, Tenn., a south-to-north displacement in ecological range of some 120 to 150 miles.

The sweet orange, *Citrus sinensis*, is a cultivated fruit tree of economic importance. Citrus trees are known to be exposed to periodic conditions of quick freezing due to unexpected frosts causing great economic costs to both producers and consumers. Although citrus flowers and fruit are most prone to frost and freeze damage, major foliar damage due to a hard freeze, especially to younger, newly expanded leaves can also cause great economic loss because weakened trees are more prone to disease and can produce less fruit the following growing season. Visual evidence from *Citrus* experiments above showing that cold-stressed leaves appear undamaged after being treated with the compositions described herein is important, but does not demonstrate that the leaves in question are physiologically viable We conducted additional experiments on this species employing a robust physiological assay of leaf viability (chlorophyll fluorescence) in tandem with a concurrent visual screening to examine the performance of both older and newly-expanded leaves by independent methods.

Chlorophyll Fluorescence Analysis

Chlorophyll fluorescence analysis is based on the fate of the excitation energy in the photosynthetic apparatus. Briefly, each quantum of light absorbed by a chlorophyll molecule raises an electron from the ground state to an excited state. The electron returns rapidly to the ground state releasing the energy through three different pathways i) photochemistry, ii) dissipation as heat and iii) fluorescence emission. Because these three processes occur in competition, any increase in the efficiency of one will result in a decrease in the yield of the other two. Therefore, determining the yield of chlorophyll fluorescence will give information about changes in the efficiency of photochemistry and heat dissipation (Maxwell et al., Chlorophyll fluorescence—a practical guide. *J. Exp. Bot.* 51:659-668 (2000)).

The photosynthetic apparatus, in particular photosystem II (PSII), is highly sensitive to stress and can be damaged before any dysfunction of plasmalemma or tonoplast becomes evident. Since chlorophyll fluorescence responds to changes in PSII photochemistry it provides a sensitive tool to evaluate plant responses to different stresses. One parameter widely used as stress indicator is $F_v/F_m$, the maximum quantum efficiency of PSII, which represents the fraction of absorbed photons that are used for photochemistry for a dark-adapted leaf. In a healthy leaf $F_v/F_m$ is about 0.6 to 0.8 and a decrease in $F_v/F_m$ is indicative of stress on PSII. Analysis of $F_v/F_m$ is commonly used in plant breeding and production programs to screen for environmental stress tolerance. Furthermore, $F_v/F_m$ analysis has shown very good correlation with field-evaluated frost damage (Rizza et al., Use of chlorophyll fluorescence to evaluate the cold acclimation and freezing tolerance of winter and spring oats. *Plant Breeding* 120: 389-396 (2001)).

Freezing tolerance of *Citrus* leaves was evaluated by chlorophyll fluorescence analysis using an OS5-FL pulse modulated fluorometer (Opti-Sciences, Hudson, N.H.). Sets of older and newly-expanded leaves (N=3 leaves of each type per experiment) were excised from *C. sinensis* trees, sprayed with tap water or Table 9, solution number 44 prior to cold-incubation at various temperatures. Following cold treatment control and treated leaves were dark-adapted for 45 min. and $F_v/F_m$ values were assessed. Measurements were taken immediately before and after (2-48 hours) the freezing treatment (30 min). $F_v/F_m$ was calculated as $(F_m-F_o)/F_m$, where $F_o$ is the minimal fluorescence of a dark-adapted leaf and $F_m$ is the maximal fluorescence of a dark-adapted leaf after a saturating flash (van Kooten et al., The use of chlorophyll fluorescence nomenclature in plant stress physiology. *Photosynthesis Research* 25:147-150 (1990)). With this assay, leaves with undamaged photosystem membranes possess Fv/Fm values of between 0.6 and 0.8 at time zero (before cold treatment) and in undamaged leaves $F_v/F_m$ values remained in this range up to 48 hours after cold treatment. In cold-damaged leaves marked reduction in Fv/Fm with time occurred, so than 24 h post-cold treatment, $F_v/F_m$ had declined to about 0.3 or lower. Thus, with this assay a judgment needs to be made on viability or mortality of an entire leaf rather than an areal percentage of viable tissue remaining, and an $F_v/F_m$ decline to a value below 0.3 at 24 hours was used as an indication that a particular leaf had become physiologically non-viable. To directly compare data from two viability methods on the same leaf, each leaf was also scored visually for % live leaf tissue remaining 24 h after cold treatment as described earlier. The composite data from these experiments are disclosed in Table 18 below.

TABLE 18

Percent viable leaf tissue area remaining after various cold treatments in old and newly-expanded leaves of *C. sinensis* sprayed with Table 9, formula 44 and assayed both by the fluorescence yield (Fv/Fm) method and a visual assay.

| Temp | Old Leaves | | | | New Leaves | | | |
|---|---|---|---|---|---|---|---|---|
| | Fv/Fm % Viable | | Visual % Viable | | Fv/Fm % Viable | | Visual % Viable | |
| °C. | control | treated | Control | treated | control | treated | control | treated |
| −5.0 | 100 | 100 | 100 | 100 | 100 | 100 | 100 | 100 |
| −5.7 | 100 | 100 | 100 | 100 | 67 | 100 | 60 | 100 |
| −6.5 | 0 | 100 | 0 | 100 | 67 | 100 | 33 | 100 |
| −7.0 | 33 | 100 | 33 | 67 | 33 | 67 | 0 | 67 |
| −7.5 | 0 | 100 | 0 | 50 | 0 | 0 | 0 | 0 |
| −8.0 | 0 | 0 | 0 | 25 | 0 | 33 | 0 | 0 |
| −8.5 | 0 | 0 | 0 | 0 | 0 | 0 | 0 | 0 |

Table 18 shows the positive effects the compositions of the present disclosure have on photosynthetic membrane stabilization in both older and newly-expanded *Citrus* leaves. Further, the effective temperature range for this protective effect, as measured by $F_v/F_m$ assays, closely resembled visual damage curves in this series of experiments and in an additional series of *Citrus* experiments shown earlier in Table 12 At minus 5.0° C., approximately the critical temperature for first foliar injury in control leaves of *Citrus*, both control specimens and those treated with composition 44 of Table 9, and both old and newly expanded leaves, displayed unchanging $F_v/F_m$ curves between at time zero (after treatment and right before cold treatment) and 2, 24, and 48 hours post treatment. $F_v/F_m$ values remained stable after minus 5.7° C. treatment in old leaves, but one of three controls, newly-expanded leaves exhibited loss of photosynthetic integrity, and visually, about 40% of the composite surface area of the three leaves was visually non-viable.

At minus 6.5° C. through minus 8.0° C., there was found to be a high degree of consistency between the visual scoring analyses used in evaluating leaves and $F_v/F_m$ for both old leaves and new leaves, and for controls and treated leaves. The treated older leaves did not lose membrane integrity until exposed to temperatures colder than minus 7.5° C. and warmer than minus 8.0° C., whereas membrane integrity in control older leaves was lost between minus 5.7° C. and minus 6.5° C. Therefore, $F_v/F_m$ measurements suggest that treatment with compositions disclosed herein induced a 1.0° C. to 2.0° C. decrease in the lethal temperature, similar to the value of 1.2° C. determined by the visual scoring described in Table 18 herein.

Taken together, the results from Tables 17 and 18 demonstrate that the compositions described herein are capable of lowering the foliar mortality temperature in *C. sinensis* leaves by approximately 1.5° C.; more than 0.25 USDA Zone equivalents. More importantly, it is somewhat common for winter minimum temperatures in citrus-growing reasons to dip below minus 5.0° C., the FDT for control leaves in the experiments and a temperature at which there was no damage to composition-treated foliage. Similarly, it is very rare for temperatures to drop below minus 7.0° C. in these regions, but when that happens it devastates extant foliage, whereas with the compositions disclosed here, viable foliage would survive down to at least minus 8.0° C. and below. The disclosed compositions provide a method for commercial (and residential) citrus growers to reduce the threat of foliar damage and complete foliar mortality in the northern and central areas of the citrus-belt.

Example 76

In addition to the laboratory experiments conducted on excised plant tissues, a series of field experiments were conducted at Miami University, Oxford, Ohio with selected whole plants during the winter of 2005 to 2006. These experiments were conducted on plants that were planted at least the spring before and therefore had become established to their soil and environment.

In one experiment, weather forecasters predicted a period of sub-freezing temperature to begin on or about the evening of Dec. 19, 2005. To test the effects of the disclosed compositions, specimens of *Trachycarpus fortunei* planted during the spring of 2005 were sprayed either with tap water (controls; N=3) or the composition 43 from Table 9 (N=3) on Dec. 15, 2005 several days before the forecasted severe cold temperature period. The air temperature at the time of spraying was measured at approximately 4° C. Aside from leaf mulching, no additional winter protection was provided to these plants. Mercury minimum/maximum temperature thermometers were positioned adjacent to the specimens of *Trachycarpus fortunei* to record local temperatures during the period of the field test.

During the overnight periods on December 19th and 20th the temperatures were recorded as low as minus 14.4° C. and minus 15.0° C., respectively. In addition, a separate calculation of the wind chill readings showed the wind chill factor for each overnight period to be well below minus 18.0° C. Monitors indicated the ambient air temperature for the period of December 15 through midday on December 21 continuously remained below freezing: 0° C.

In addition, snowfall occurred twice during this period. The effect of this snowfall was that some of the foliage of smaller specimens of *Trachycarpus fortunei* became covered by an insulating layer of snow. This foliage was considered to be compromised and, therefore, these plants were marked accordingly so that the snow-covered foliage would be excluded from later analysis. After the period of below freezing temperatures, ambient air temperatures rose occasionally to as high as 15° C. This period of higher temperatures also coincided with periods of both rain and freezing rain.

The evaluation of foliar damage was conducted on all treated specimens of *Trachycarpus fortunei* on Jan. 4, 2006.

This corresponded to a period of approximately 14 days after the period of continuous freeze conditions and 21 days after the specimens of *Trachycarpus fortunei* were treated. Foliage of the control specimens of *T. fortunei* not covered by insulating snow suffered near complete to complete mortality manifested by brown-colored leaves down to the petiole bases (i.e., a rating of 6 in the FDI). In contrast, the exposed foliage of specimens that were treated with the solution 44 exemplified in Table 9 were judged to be largely undamaged (FDI=2 to 3). One of the treated specimens that was not subject to any accumulating snow cover and therefore completely exposed to the extreme conditions of cold temperatures suffered approximately 5% foliar burn (tip and margin burn). Similarly, in the other two treated specimens foliar burn in exposed leaves was less than 30%.

In addition, the treated specimens continued to display green foliage through January and into February 2006, during which time several overnight lows were measured in the range of minus 12° C. These data indicate that the treatment of the *Trachycarpus fortunei* specimens provided extended freeze death protection, in spite of the precipitation that occurred during this period prior to evaluation on Jan. 4, 2006.

A further series of field experiments were conducted on the species *Musa basjoo*, a variety of banana known to have a low tolerance to freezing temperatures. Specimens of *Musa basjoo* were potted in 1-quart containers and incubated outdoors under subfreezing conditions. Half the specimens were treated with composition 42 from Table 9 and allowed to air dry for 30 minutes then placed outdoors for 3 hours where the recorded air temperature ranged from minus 2.8° C. to minus 3.3° C. The treated specimens exhibited between 50% to 60% foliar burn, whereas the control specimens sprayed with tap water were completely killed within minutes at these temperatures. In a further trial, treated specimens of *Musa basjoo* exhibited only minor foliar damage (minor margin and tip burn) when exposed to temperatures as low as minus 3.5° C. for up to 30 minutes, which was a result consistent with the laboratory observations. This confirmed the laboratory procedures to be predictive of real world application.

In a further collaborating test, *M. basjoo* specimens were treated and incubated overnight outdoors where the recorded air temperatures dropped as low as minus 1.4° C. and remained below 0° C. for approximately 9 hours. Untreated controls suffered between 60% and 70% foliar damage whereas the specimens treated with composition 41 of Table 9 were undamaged.

These field results with *Musa basjoo*, a tender ornamental species easily damaged by even modest cold, are highly significant from a horticulturalist's standpoint. These experiments suggest that applying a composition formulated according to the present disclosure, that *Musa basjoo* can be successfully maintained with minimal foliar damage through even hard freeze conditions in temperature conditions ranging as low as minus 5° C. The disclosed compositions provide a significant advantage to homeowners, landscape professionals, and commercial growers who wish to cultivate *Musa basjoo* in areas that are subject to freezing temperatures.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. A plant cryoprotection composition comprising:
   a) from 0.8% to 8% by weight of one or more extracellular desiccants;
   b) from 0.01% to 1.0% by weight of one or more intracellular cryoprotectants;
   c) from 0.02% to 0.5% by weight of one or more surface active agents;
   d) from 0.1% to 3% by weight of one or more anti-transpirants;
   e) from 0.1% to 3% by weight of one or more sources of silicate; and
   f) at least 70% by weight of water.

2. The composition according to claim 1, comprising from 2% to 5% by weight, of one or more extracellular desiccants.

3. The composition according to claim 1, comprising from 1% to 6% by weight, of one or more extracellular desiccants.

4. The composition according to claim 1, wherein the one or more extracellular desiccants comprise one or more polyethylene glycols having the formula:

$$HO(CH_2CH_2O)_xH$$

wherein x is from 4 to 460.

5. The composition according to claim 4, wherein the polyethylene glycol has an average molecular weight of from 3,000 g/mol to 12,000 g/mol.

6. The composition according to claim 5, wherein the polyethylene glycol has an average molecular weight of from 4,000 g/mol to 10,000 g/mol.

7. The composition according to claim 6, wherein the polyethylene glycol has an average molecular weight of 8,000 g/mol.

8. The composition according to claim 1, wherein extracellular desiccants comprise one or more polypropylene glycols.

9. The composition according to claim 1, comprising from 0.03% to 0.07% by weight, of one or more intracellular cryoprotectants.

10. The composition according to claim 1, comprising from 0.045% to 0.055% by weight, of one or more intracellular cryoprotectants.

11. The composition according to claim 1, comprising from 0.02% to 0.05% by weight of one or more intracellular cryoprotectants.

12. The composition according to claim 1, wherein the intracellular cryoprotectant is a polyol having the formula:

$$HOCH_2-[CHOH]_x-CH_2OH$$

wherein x is from 1 to 20.

13. The composition according to claim 1, wherein the intracellular cryoprotectant is a polyol chosen from glycerol, (2R,3R)-butane-1,2,3,4-tetraol, (2S,3R)-butane-1,2,3,4-tetraol, (2R,3S)-butane-1,2,3,4-tetraol, (2S,3S)-butane-1,2,3,4-tetraol, (2R,3R,4R)-pentane-1,2,3,4,5-pentaol, (2S,3R,4R)-pentane-1,2,3,4,5-pentaol, (2R,3S,4R)-pentane-1,2,3,4,5-pentaol, (2R,3R,4S)-pentane-1,2,3,4,5-pentaol, (2S,3S,4R)-pentane-1,2,3,4,5-pentaol, (2S,3R,4S)-pentane-1,2,3,4,5-pentaol, (2R,3S,4S)-pentane-1,2,3,4,5-pentaol, and (2S,3S,4S)-pentane-1,2,3,4,5-pentaol.

14. The composition according to claim 1, wherein the intracellular cryoprotectant is glycerol.

15. The composition according to claim 1, wherein the extracellular desiccant lowers the cell water content via cytorrhysis rather than by plasmolysis.

16. The composition according to claim 1, wherein at least one of the surface active agents is a heptamethyl-trisiloxane having the formula:

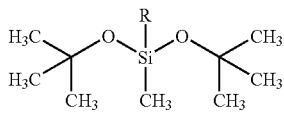

wherein R is a hydrophobic unit comprising ethyleneoxy units, propyleneoxy units, or mixtures of ethyleneoxy and propyleneoxy units; and the heptamethyl-trisiloxane has a molecular weight of from 500 g/mol to 30,000 g/mole.

17. The composition according to claim 1, wherein the surface active agent comprises 100% ethyleneoxy units and an average molecular weight of 600 g/mol.

18. The composition according to claim 1, wherein the surface active agent comprises 60% ethyleneoxy units and 40% propyleneoxy units and an average molecular weight of 600 g/mol.

19. The composition according to claim 1, wherein at least one of the surface active agents is an ethoxylated alcohol having the formula:

wherein R is a linear or branched alkyl group having from 6 to 20 carbon atoms and n is an integer from 2 to 20.

20. The composition according to claim 1, wherein at least one of the surface active agents is an amide that is ethoxylated, propoxylated, or comprises mixtures thereof, having the formula:

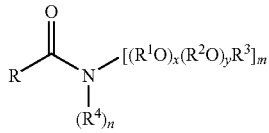

wherein R is $C_7$-$C_{21}$ linear alkyl, $C_7$-$C_{21}$ branched alkyl, $C_7$-$C_{21}$ linear alkenyl, or $C_7$-$C_{21}$ branched alkenyl; $R^1$ is ethylene; $R^2$ is $C_3$-$C_4$ linear alkylene, $C_3$-$C_4$ branched alkylene, or mixtures thereof; $R^3$ is hydrogen, $C_1$-$C_4$ linear alkyl, or $C_3$-$C_4$ branched alkyl; $R^4$ is hydrogen, $C_1$-$C_4$ linear alkyl, or $C_3$-$C_4$ branched alkyl; m is 1 or 2, n is 0 or 1, provided that when m is equal to 1, n is equal to 1; and when m is 2, n is equal to 0; x is from 0 to 50; y is from 0 to 10.

21. The composition according to claim 1, comprising from 0.1% to 2% by weight of one or more anti-transpirants.

22. The composition according to claim 1, wherein the anti-transpirant is a terpenoid monomer or dimer that upon exposure to sunlight forms a polymeric film.

23. The composition according to claim 1, wherein the anti-transpirant is di-1-menthene.

24. The composition according to claim 1, wherein the anti-transpirant is a homopolymer or co-polymer formed from one or more monomers having the formula:

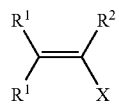

wherein each $R^1$ is independently hydrogen, $C_1$-$C_{12}$ alkyl, $C_1$-$C_{12}$ alkoxy, phenyl, substituted phenyl, benzyl, substituted benzyl, carbocyclic, heterocyclic, or mixtures thereof; $R^2$ is hydrogen, halogen, $C_1$-$C_{12}$ alkyl, $C_1$-$C_{12}$ alkoxy, phenyl, substituted phenyl, benzyl, substituted benzyl, carbocyclic, heterocyclic, or mixtures thereof; X is hydrogen, hydroxyl, halogen, —$(CH_2)_mCH_2OH$, —$(CH_2)_mCOR$, or —$(CH_2)_mCH_2OCOR'$ wherein R is OR', —$N(R')_2$, or —$(CH_2)_nN(R'')_2$; each R' is independently hydrogen, $C_1$-$C_8$ alkyl, $C_2$-$C_8$ hydroxyalkyl, or —$(CH_2)_nN(R'')_2$; R'' is independently hydrogen, or $C_1$-$C_4$ alkyl; m is from 0 to 6, and n is from 2 to 6.

25. The composition according to claim 1, wherein the anti-transpirant is formed from a monomer chosen from ethylene, propylene, butylene, styrene, vinyl alcohol, crotyl alcohol, acrylic acid, styrylacetic acid, methacrylic acid, crotonic acid, 3,3-dimethyl-acrylic acid, methyl acrylate, ethyl acrylate, n-propyl acrylate, isopropyl acrylate, butyl acrylate, methyl methacrylate, ethyl methacrylate, n-propyl methacrylate, isopropyl methacrylate, butyl methacrylate, methyl 3,3-dimethyl-acrylate, ethyl 3,3-dimethyl-acrylate, n-propyl 3,3-dimethyl-acrylate, isopropyl 3,3-dimethyl-acrylate, butyl 3,3-dimethyl-acrylate, acrylamide, N-methyl acrylamide, N,N-dimethyl acrylamide, N-(aminoethyl)methyl acrylamide, and vinyl acetate.

26. The composition according to claim 1, comprising from 0.1% to 2% by weight of one or more sources of silicate.

27. The composition according to claim 1, wherein the source of silicate is chosen from potassium silicate, sodium silicate, lithium silicate, calcium silicate, and ammonium silicate.

28. The composition according to claim 1, wherein the source of silicate is a solution comprising 29.1% of the potassium salt of silicic acid and 70.9% water.

29. The composition according to claim 1, wherein the source of silicate is a solid material comprising 71.0% $SiO_2$ and 28.4% $K_2O$.

30. A composition comprising:
a) from 0.8% to 8% by weight of one or more polyethylene glycols having the formula:

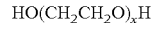

wherein x is from 4 to 460;
b) from 0.01% to 1.0% by weight of a polyol having the formula:

wherein x is from 1 to 20;
c) from 0.02% to 0.5% by weight of a heptamethyl-trisiloxane having the formula:

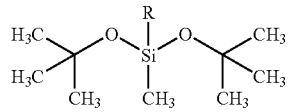

wherein R is a hydrophobic unit comprising ethyleneoxy units, propyleneoxy units, or mixtures of ethyleneoxy and propyleneoxy units; and the molecular weight of the heptamethyl-trisiloxane is from 500 g/mol to 30,000 g/mole;

d) from 0.1% to 3% by weight of di-1-menthene;

e) from 0.1% to 3% by weight of potassium silicate; and f) at least 70% by weight of water.

31. The composition according to claim 30, wherein the polyethylene glycol is chosen from PEG 4000, PEG 5000, PEG 6000, PEG 7000, and PEG 8000.

32. The composition according to claim 30, wherein the polyethylene glycol is PEG 8000.

33. The composition according to claim 30, wherein the polyol is glycerol.

34. The composition according to claim 30, wherein the heptamethyl-trisiloxane has the formula:

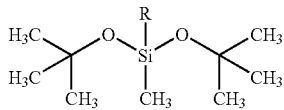

wherein R is a hydrophobic unit comprising ethyleneoxy units, and wherein the heptamethyl-trisiloxane has a molecular weight of 600 g/mole.

35. A composition according to claim 1, comprising:

from about 0.8% to about 8% by weight of one or more extracellular desiccants;

a) 0.5% by weight of one or more intracellular cryoprotectants;

b) 0.1% by weight of one or more surface active agents;

c) 2% by weight of one or more anti-transpirants;

d) 0.5% by weight of one or more sources of silicate; and e) at least 70% by weight of water.

36. A method for providing cryoprotection to plants comprising applying the composition according to claim 1, to a plant in need of cryoprotection.

37. A method for providing cryoprotection to plants comprising applying the composition according to claim 30, to a plant in need of cryoprotection.

38. A method for lowering a plant's foliar damage threshold comprising applying to the plant a composition according to claim 1.

39. A method for lowering a plant's foliar damage threshold comprising applying to the plant a composition according to claim 30.

40. The method according to claim 38, wherein the plant's foliar damage threshold is lowered by at least 1° C.

41. The method according to claim 38, wherein the plant's foliar damage threshold is lowered by at least 1.5° C.

42. The method according to claim 38, wherein the plant's foliar damage threshold is lowered by at least 2° C.

43. The method according to claim 38, wherein the plant's foliar damage threshold is lowered by at least 2.5° C.

44. The method according to claim 38, wherein the plant's foliar damage threshold is lowered by at least 3° C.

45. A method for lowering a plant's foliar mortality threshold comprising applying to the plant a composition according to claim 1.

* * * * *

UNITED STATES PATENT AND TRADEMARK OFFICE
CERTIFICATE OF CORRECTION

| | | |
|---|---|---|
| PATENT NO. | : 8,580,708 B2 | Page 1 of 1 |
| APPLICATION NO. | : 12/664968 | |
| DATED | : November 12, 2013 | |
| INVENTOR(S) | : Francko et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 542 days.

Signed and Sealed this
Twenty-fourth Day of March, 2015

Michelle K. Lee
*Director of the United States Patent and Trademark Office*